United States Patent [19]

Gimbrone, Jr. et al.

[11] Patent Number: 5,302,384

[45] Date of Patent: Apr. 12, 1994

[54] ENDOTHELIAL-DERIVED IL-8 ADHESION INHIBITOR

[75] Inventors: Michael A. Gimbrone, Jr., Jamaica Plain, Mass.; M. Elyse Wheeler, Diamond Head, Ariz.

[73] Assignee: Brigham and Women's Hospital, Boston, Mass.

[21] Appl. No.: 28,705

[22] Filed: Feb. 25, 1993

Related U.S. Application Data

[63] Continuation of Ser. No. 442,786, Nov. 29, 1989, abandoned, which is a continuation-in-part of Ser. No. 232,224, Aug. 15, 1988, abandoned.

[51] Int. Cl.$^5$ .............................................. A61K 45/05
[52] U.S. Cl. .................................. 424/85.2; 530/351; 514/21
[58] Field of Search ..................... 530/351; 424/85.2; 514/21

[56] References Cited

U.S. PATENT DOCUMENTS

| | | | |
|---|---|---|---|
| 4,571,382 | 2/1986 | Adachi | 435/7 |
| 4,797,277 | 1/1989 | Arfors | 424/85.8 |
| 4,840,793 | 6/1989 | Todd, III et al. | 424/85.8 |
| 4,897,348 | 1/1990 | Johnson et al. | 435/69.1 |

FOREIGN PATENT DOCUMENTS

WO89/04836  6/1989  World Int. Prop. O.

OTHER PUBLICATIONS

BACHEM Biosciences, Inc., *Lymphokine Bulletin Information Sheet*, Feb. 1991 (BA 054).

Bevilacqua et al., "Identification of an inducible endothelial-leukocyte adhesion molecule", *Proc. Natl. Acad. Sci. USA* 84:9238-9242 (Dec. 1987).

Bevilacqua et al., "Identification of an inducible endothelial-leukocyte adhesion molecule (E-LAM 1) using monoclonal antibodies (Mab)", *Fed. Proc.* 46(3):405, Abstract No. 514 (Mar. 29-Apr. 2, 1987).

Bevilacqua et al., "Interleukin 1 acts on cultured human vascular endothelium to increase the adhesion of polymorphonuclear leukocytes, monocytes, and related leukocyte cell lines", *J. Clin. Invest.* 76:2003-2011 (Nov. 1985).

Bevilacqua et al., "Interleukin-1 activation of vascular endothelium-effects on procoagulant activity and leukocyte adhesion", *Am. J. Pathol.* 121(3): 394-403 (Dec. 1985).

Clore, G.M. et al., "Determination of the secondary structure of interleukin-8 by neclear magnetic resonance spectroscopy", *J. of Biological Chemistry* 264(32):18907-18911 (Nov. 15, 1989).

Dahinden, C. A. et al., "The neutrophil-activating peptide NAF/NAP-1 induces histamine and leukotriene release by interleukin 3-primed basophils", *J. Exp. Med.* 170:1787-1792 (Nov. 1989).

Denton, M. D. et al., "Cytokine-induced phagocyte adhesion to human mesangial cells: role of CD11/CD18 integrins and ICAM-1", *Am. J. Physiol.* 261:F1071-F1079 (1991).

Furuta, R. et al., "Production and characterization of recombinant human neutrophil chemotactic factor", *J. Biochem.* 106:436-441 (1989).

Harlan, J. M., "Leukocyte-endothelial interactions", *Blood* 65(3):513-525 (Mar. 1985).

Korthuis, R. J. et al., "Leukocyte depletion attenuates vascular injury in postischemic skeletal muscle", *Am. J. Physiol.* 254:H823-H827 (1988).

Kowalski, J. and Denhardt, D. T., "Regulation of the mRNA for monocyte-derived neutrophil-activating peptide in differentiating HL60 promyelocytes", *Molecular and Cellular Biol.* 9(5):1946-1957 (May 1989).

Larsen, C. G. "Production of interleukin-8 by human dermal fibroblasts and keratinocytes in response to interleukin-1 or tumour necrosis factor", *Immunology* 68:31-36 (1989).

Larsen, C. G. et al., "The neutophil-activating protein (NAP-1) is also chemotactic for T lymphocytes", *Science* 243:1464-1466 (Mar. 17, 1989).

Lee, T. H. et al., "Isolation and characterization of eight tumor necrosis factor-induced gene sequences from human fibroblasts", *Mol. Cell. Biol.* 10:1982-1988 (1990).

Matsushima, K. et al., "Molecular cloning of a human monocyte-derived neutrophil chemotactic factor (MDNCF) and the induction of MDNCF mRNA by interleukin 1 and tumor necrosis factor", *J. Exp. Med.* 167:1883-1893 (Jun. 1988).

Miller, H. I. et al., "Cloning and expression of a yeast ubiquitin-protein cleaving activity in *Escherichia coli*", *Bio/Technology* 7:698-704 (Jul. 1989).

Modi, W. S. et al., "Monocyte-derived neutrophil chemotactic factor (MDNCF/IL-8) resides in a gene cluster along with several other members of the platelet factor 4 gene superfamily", *Human Genetics* 84:185-187 (1990).

Mukaida, N. et al., "Genomic structure of the human monocyte-derived neutrophil chemotactic factor IL-8", *J. of Immunology* 143(4):1366-1371 (Aug. 15, 1989).

Mullenbach, G. T. et al., "Chemical systhesis and expression in yeast of a gene encoding connective tissue activating peptide-III", *J. of Biological Chemistry* 261(2):719-722 (Jan. 15, 1986).

Pober et al., "Activation of cultured human endothelial cells by recombinant lymphotoxin:Z comparison with (List continued on next page.)

Primary Examiner—Michael G. Wityshyn
Assistant Examiner—Choon P. Koh
Attorney, Agent, or Firm—Sterne, Kessler, Goldstein & Fox

[57] ABSTRACT

The present invention relates to intercellular adhesion inhibitory factors produced by cytokine activated endothelial cells. These factors designated endothelial-derived IL-8 find use in the diagnosis and treatment of inflammation and in the protection of endothelial cells from neutrophil mediated damage.

6 Claims, 12 Drawing Sheets

OTHER PUBLICATIONS tumor necrosis factor and interleukin 1 species", *J. of Immunology* 138:3319-3324 (May 15, 1987).

Pober, J. S. and Cotran, R. S., "The role of endothelial cells in inflammation", *Transplantation* 50(4):537-544 (Oct. 1990).

Schmid, J. and Weissmann, C., "Induction of mRNA for a serine protease and a $\beta$-thromboglobulin-like protein in mitogen-stimulated human leukocytes", *J. of Immunology* 139(1):250-256 (Jul. 1, 1987).

Schröder, J. M., "The monocyte-derived neutrophil activating peptide (NAP/interleukin 8) stimulates human neutrophil arachdonate-5-lipoxygenase, but not the release of cellular arachidonate", *J. Exp. Med.* 170:847-863 (Sep. 1989).

Strieter, R. M. et al., "Endothelial cell gene expression of a neutrophil chemotactic factor by TNF-$\alpha$, LPS, and IL-1$\beta$", *Science* 243:1467-69 (Mar. 17, 1989).

Suzuki, K. et al., "Localization of chemotactic activity and 64 kD protein phosphorylation for human polymorphonuclear leukocytes in N-terminus of the chemotactic protein LUCT/IL-8#", *Biochem. and Biophys. Res. Commun.* 163(3):1298-1305 (Sep. 29, 1989).

Van Damme, J. et al., "Purification of granulocyte chemotactic peptide/interleukin-8 reveals N-terminal sequence heterogeneity similar to that of $\beta$-thromboglobulin", *Eur. J. Biochem.* 181:337-344 (1989).

Van Damme, J. et al., "The chemotactic activity for granulocytes produced by virally infected fibroblasts is identical to monocyte-derived interleukin 8", *Eur. J. Immunol.* 19:1189-1194 (1989).

Van Damme, J. et al., "A novel, NH$_2$-terminal sequence-characterized human monokine possessing neutrophil chemotactic, skin-reactive, and granulocytosis-promoting activity", *J. Exp. Med.* 167:1364-1376 (Apr. 1988).

Wheeler et al., *Fed. Proc.* 45:450, "Interleukin-1 treated endothelial cells produce an inhibitor of leukocyte-endothelial adhesion", Abstract No. 1725 (Feb. 21, 1986).

Wheeler et al., *Fed. Proc.* 46(3):758, "Characterization of an endothelial-derived inhibitor of leukocyte adhesion", Abstract No. 2577 (Feb. 24 or Mar. 1, 1987).

Willems, J. et al., "Human granulocyte chemotactic peptide (IL-8) as a specific neutrophil degranulator: comparison with other monokines", *Immunology* 67:540-542 (1989).

Tonnesen et al. (1986) Adv. Inflammation Res. 10:288-291.

McCord et al. (1986) Adv. Inflammation Res. 10:21-29.

Strieter et al. (1988, Nov. 15) Biochem Brophy Res Comm 156(3):1340;14 1345.

Zimmerman et al. (1985) J. Immunology 134(3):1866-1874.

Sofer et al. (1983) Biotechniques 1(4):198-203.

Wheeler et al. (1987, Mar. 1) Fed. Proc. 46(3):758.

Yoshimura et al. (Aug. 1, 1987) J. Immunology 139(3):788-793.

Schroder et al. (1987, Nov. 15) J. Immunology 139(10):3474-3483.

Gregory et al. (1988, Mar. 15) Biochem Biophys Res Comm 151(2):883-890.

Herbert et al. (1990) J. Immunology 145(9):3033-3040.

Lindley et al. (1988, Dec.) Proc. Natl. Acad. Sci. U.S.A. 85:9199-9203.

Walz et al. (1987, Dec. 16) Biochem. Biophys. Res. Comm. 149(2):755-761.

Yoshimura et al. (1987, Dec.) Proc. Natl. Acad. Sci. U.S.A. 84:9233-9237.

Wolpe et al. (1988, Feb.) J. Exp. Med. 167:570-581.

Hoover et al., *J. Cell Biol.* 95:10A (1982).

Basford et al., *Blood* 68:79a (1986).

Harlan et al., *Blood* 66:167-178 (1985).

Zimmerman et al., *J. Immunol.* 134:1866-1874 (1985).

Kerr et al., *J. Cell. Biol. (Suppl.)*:471a (1986).

Cronstein et al., *J. Clin. Invest.* 78:760-770 (1986).

Wheeler et al., *Fed. Proc.* 45:450 (1986).

Wheeler et al. *Fed Proc.* 46:758 (1987).

Varani et al., *Laboratory Investigation* 59:292 (1988).

Baggiolini et al., *J. Clin. Invest.* 84:1045-1049 (1989).

Hechtman et al., *J. Immunology* 147(3):883-892 (1991).

ENDOTHELIAL-DERIVED IL-8 ADHESION INHIBITOR

STATEMENT AS TO RIGHTS TO INVENTIONS MADE UNDER FEDERALLY SPONSORED RESEARCH AND DEVELOPMENT

Part of the work leading to this invention utilized U.S. Government funds. The U.S. Government has certain rights in this invention.

This application is a continuation of U.S. application Ser. No. 07/442,786, filed Nov. 29, 1989, now abandoned, which is a continuation in part of U.S application Ser. No. 07/232,224, filed Aug. 15, 1988, now abandoned.

BACKGROUND OF THE INVENTION

1. Field of the Invention

The present invention is drawn to endothelial-derived interleukin-8 (IL-8). These polypeptides, previously identified as "leukocyte adhesion inhibitor" (LAI), are involved in the process through which populations of leukocytes are inhibited from adhering to cellular substrates. The invention additionally relates to the use of endothelial-derived IL-8 as anti-inflammatory agents and as therapeutics for clinical indications in which damage of vascular endothelium and other tissues occurs.

2. Description of the Related Art

When foreign invaders such as bacteria, viruses or other invading parasites penetrate the skin or mucous membranes, cellular defense mechanisms are immediately induced. Local and blood-borne monocytes and polymorphonuclear leukocytes (PMN), two of the phagocytic-type cells of the defense system, accumulate around the invaders and initiate phagocytosis. An excellent review of the defense system is provided by Eisen, H. W., In: *Microbiology*, Third Ed., Harper and Row, Philadelphia, Pa. (1980), pp. 290–295 and 381–418.

The presence of such foreign entities results in an inflammatory response characterized by (1) dilation of surrounding blood vessels; (2) an increase in vascular permeability; and (3) diapedesis, the migration of monocytes and PMN across vascular walls.

The accumulation of blood leukocytes at sites of inflammation and injury depends upon their localized adhesion to the vascular lining. Localized adhesion is essential in a variety of pathophysiological processes. Leukocytes must be able to attach to cellular substrates in order to properly defend the host against these invaders. They must also attach to endothelial cells so that they can migrate from the circulation to sites of ongoing inflammation. Furthermore, they must attach to antigen-presenting cells so that a specific immune response can occur. Finally, they must attach to appropriate target cells so that lysis of virally-infected or tumor cells can occur.

The adherence of leukocytes to vascular endothelium in areas of inflammation and injury has long been known. It has also long been suspected that molecular changes in the blood vessel wall are involved in these endothelial-leukocyte interactions. However, experimental evidence supporting this concept was lacking until recently (see Harlan, J., *Blood* 65:513-525 (1985)).

Recent studies have demonstrated that certain inflammatory cytokines such as Interleukin-I (IL-1) (see, e.g., Bevilacqua et al., *J. Clin. Invest.* 76:2003–2011 (1985); Bevilacqua et al., In: *Leukocyte Emigration and Its Sequelae*, S. Karger, AG, Basel and New York, pp. 79–93 (1986); Dunn et al., In: *The Physiologic, Metabolic, and Immunologic Actions of Interleukin-1*, Alan R. Liss, Inc., New York, pp. 45–59 (1985); Schleimer et al., *J. Immunol.* 136:649–654 (1986); Gamble et al., *PNAS U.S.A.* 82:8667–8671 (1985); Pohlman et al., *J. Immunol.* 136:4548–4553 (1986) ; Cavender et. al., *Fed. Proc.*, 46:113–117 (1987)), tumor necrosis factor (TNF) (Gamble et al., *PNAS U.S.A.* 82:8667–8671 (1985)), and Gram-negative bacterial endotoxin (lipopolysaccharide) (LPS) (Schleimer et al., (1986); Pohlman et al., *J. Immunol.* 136:4548–4553 (1986)) can act directly on vascular endothelium in vitro to increase the adhesiveness of the endothelial cell surface for blood leukocytes as well as the related leukocyte cell lines (HL-60 and U937).

Other chemotactic factors, such as purified complement components, formyl-methionyl-leucyl-phenylalanine, and leukotriene $B_4$ can also augment the attachment of PMN to cultured endothelial monolayers (see, e.g., Smith et al., *Exp. Cell Res.* 122:169–177 (1979); Hoover et al., *J. Cell Sci.* 45:73–86 (1980); Hoover et al., *PNAS U.S.A.* 81:2191–2193 (1984); Zimmerman et al., *Thromb. Res.* 35:203–217 (1984); Gimbrone et al., *J. Clin. Invest.* 74:1552–1555 (1984); Tonnesen et al., *J. Clin. Invest.* 74:1581–1592 (1984); Charo et al., *Blood* 65:473–479 (1985); Harlan et al., *Lab. Invest.* 52:141–150 (1985)). The relative significance of endothelial versus leukocyte responses, and the cellular mechanisms involved in their adhesion, however, are still largely unknown.

The inhibition of leukocyte adhesion potentially is of central importance to therapeutic interventions in inflammatory disease processes. Although leukocyte adhesion is normally desirable, it is also implicated in immune and non-immune inflammatory disease processes, including organ transplant rejection, tissue graft rejection, allergic reactions, autoimmune diseases, rheumatoid arthritis, vasculitis, septic shock, adult respiratory distress syndrome (ARDS), glomerulonephritis, and other tissue or organ specific forms of acute and chronic inflammation. Further, in the setting of ischemiareperfusion, leukocyte adhesion may produce microvascular occlusion, tissue injury and death. Hence, any means capable of attenuating or inhibiting cellular adhesion would be highly desirable for certain patients.

DEFINITIONS

For brevity, the following abbreviations are used through-out this application: CM, conditioned media; FCS, fetal calf serum; HEC, human umbilical vein endothelial cell(s); TIS, transferrin/insulin/selenium; hmIL-1, human monocyte-derived interleukin 1; rIL-1, recombinant IL-1; RTNF, recombinant tumor necrosis factor; LPS, Gram-negative bacterial endotoxin; LAI, leukocyte adhesion inhibitor; PMN, polymorphonuclear leukocyte(s); GM-GSF, granulocyte-monocyte colony stimulating factor; FMLP, N-formyl-methionyl-leucyl-phenylalanine; $LTB_4$, leukotriene $B_4$; PMA, phorbol 12-myristate 13-acetate.

Information Disclosure Statement

U.S. application Ser. No. 07/232,224 was drawn to a leukocyte adhesion inhibitor, LAI. Subsequent studies have indicated that LAI comprises a mixture of polypeptides, one of which is interleukin-8, IL-8, a 72-amino acid neutrophil activating polypeptide secreted by activated T cells and monocytes. Hence, the present application refers to LAI as "endothelial-derived IL-8."

The following documents relate to the present invention and are incorporated herein by reference.

Hoover et al., *J. Cell Biol.* 95:10A (1982) and Basford et al., *Blood* 68:79a (1986) disclose that conditioned media from unstimulated human and bovine endothelial cells produce an attenuation of superoxide production by stimulated neutrophils.

Harlan et al., *Blood* 66:167–178 (1985) disclose that the monoclonal antibody to the CDw18 complex (the leukocyte surface differentiation antigen complex) produces a significant inhibition of agonist-induced polymorphonuclear leukocyte adhesion.

Zimmerman et al., *J. Immunol.* 134:1866–1874 (1985) disclose that prostaglandin metabolites of endothelial cells inhibit several leukocyte functions, including adhesion.

Kerr et al., *J. Cell Biol.* 103:1760 (1986) disclose that exposure of polymorphonuclear leukocytes to unstimulated endothelial cells or medium conditioned by these cells inhibits adhesion of leukocytes to unstimulated endothelial monolayers and tissue culture plastic.

Cronstein et al., *J. Clin. Invest.* 78:760–770 (1986) disclose that adenosine and its analogue 2-chloroadenosine inhibit the adherence of N-formylmethionyl-leucyl-phenylalanine stimulated neutrophils to cultured human umbilical vein endothelial cells.

Wheeler et. al., *Fed. Proc.*. 45:450 (1986) and Wheeler et al., in a poster session at the 4th Int'l. Symposium on the Biology of the Vascular Endothelial Cell, in August 1986, in the Netherlands, disclose that interleukin-1-treated endothelial cells produce an inhibitor of leukocyte-endothelial adhesion.

Wheeler et al., *Fed. Proc.* 46:758 (1987) disclose some characteristics of a natural form of the endothelial-derived inhibitor of leukocyte adhesion.

Varani et al., *Laboratory Investigation* 59:292 (1988), disclose that pretreatment of rat endothelial cells with TNF increases their susceptibility to killing by activated human neutrophils.

SUMMARY OF THE INVENTION

The present invention is drawn to factors produced by endothelial cells, in particular, human umbilical vein endothelial cells, treated with IL-1, TNF, or LPS. These factors are non-cyclooxygenase-derived inhibitors which act to block PMN and monocyte adhesion, but not lymphocyte adhesion, to the hyperadhesive (cytokine-stimulated) endothelial surface. Production of these inhibitory factors is not limited to human umbilical vein endothelial cells but includes cell types including $SV_{40}$ virally transformed human umbilical vein endothelial cells and human diploid skin fibroblasts. These factors designated endothelial-derived IL-8 find use as leukocyte adhesion inhibitor molecules and as agents which protect endothelial cells from neutrophil mediated damage. The compositions of these factors and methods for their use are provided.

Substantially pure endothelial-derived IL-8, encompassed by the present invention, comprises a mixture of at least two unique polypeptides designated [Ala IL-8]$_{77}$ and [Ser IL-8]$_{72}$. This material inhibits both monocyte and neutrophil adhesion to cytokine activated endothelial cultures. However, highly purified endothelial-derived IL-8 and recombinant human [Ala IL-8]$_{77}$ and [Ser IL-8]$_{72}$ do not inhibit adhesion monocycle. Therefore, natural preparations of endothelial-derived IL-8 may contain other leukocyte adhesion inhibiting activity, or activities, that are active on blood monocytes.

The action of this endothelial-derived IL-8 (LAI) appears to be selectively directed at the leukocyte. However, it does not produce a global inhibition of leukocyte responsiveness to soluble inflammatory stimuli, such as formyl-methionyl-leucylphenylalanine, leukotriene $B_4$, or phorbol 12-myristate 13-acetate. It appears, instead, that this newly discovered inhibitory molecule plays a role in the modulation of leukocyte-vessel wall interactions at the very sites of inflammation and/or injury.

Specifically, cytokine- and bacterial endotoxin-stimulated human endothelial cultures generate endothelial-derived IL-8 which is a soluble, natural product of the activated endothelial cell. Its generation appears to require de novo protein synthesis but is not dependent on the cyclooxygenase pathway. Endothelial-derived IL-8 activity is stable under physiological conditions as well as extremes of temperature and pH. This thermo- and acid-stability and the lack of influence of aspirin treatment at concentrations which ablate prostacyclin production distinguish endothelial-derived IL-8 from the prostaglandin metabolites of endothelial cells which have been shown to inhibit several leukocyte functions including adhesion (Zimmerman et al., *J. Immunol.* 134:1866–1874 (1985)).

No detectable endothelial-derived IL-8 activity is found in conditioned medium from untreated endothelial cultures. This is in contrast to the report that exposure of PMN to unstimulated endothelial cells or medium conditioned by these cells inhibited the adhesion of PMN to unstimulated endothelial monolayers and tissue culture plastic (Kerr et al., *J. Cell Biol.* 103:971a (1986)). Conditioned media from unstimulated human and bovine endothelium also produce an attenuation of superoxide production by stimulated neutrophils (see Basford et al., *Blood* 68:79a (1986); Harlan et al., *Blood* 66:167–178 (1985)). In contrast, endothelial-derived IL-8 appears to selectively block leukocyte adhesion without producing a global inhibition of leukocyte function, including agonist-stimulated changes in cytosolic calcium concentrations and superoxide production.

The inventors have also demonstrated that endothelial-derived IL-8 can reverse the strong attachment of human PMN to cytokine-activated human umbilical vein endothelial cells. That is, when endothelial-derived IL-8 is added to PMN which are adherent to the activated endothelial cell, the PMN release from the endothelial cell surface. The kinetics of this "release" is rapid (1–5 minutes) and potentially reversible.

The differential effects of endothelial-derived IL-8 on leukocyte adhesion, that is, the significant inhibition of PMN, but not monocyte or lymphocyte adhesion, suggests that the action of endothelial-derived IL-8 may be related to distinct leukocyte receptors which recognize the hyperadhesive endothelial cell surface. Similarly, the lack of effect on the promyelocytic cell line HL-60 and the monocyte-like line U937 suggests that endothelial-derived IL-8 may be directed at functions or surface structures of the mature leukocyte which are deficient in this undifferentiated cell line. PMN adhesive interactions with endothelium have been demonstrated to involve the leukocyte surface differentiation antigen complex, CDw18 (LFA-1, Mac-1, p150,95) (Gamble et al., *PNAS U.S.A.* 82:8667–8671 (1985); Pohlman et al., *J. Immunol.* 136:4548–4553 (1986)). In the presence of concentrated endothelial-derived IL-8 (up to 5x relative concentration), adhesion of PMN activated with FMLP, LTB$_4$, or PMA (see Definitions, below) to control endothelial monolayers is not inhibited. In contrast, monoclonal antibodies to CDw18 complex produce significant inhibition of agonist-induced PMN adhesion (Harlan et al., *Blood* 66:167–178 (1985)). In addition, endothelial-derived IL-8 inhibition of PMN adhesion appears to be specific for the "hyperadhesive" endothelial cell surface because adhesion of PMN to serum-coated tissue culture plastic is not altered by the presence of endothelial-derived IL-8.

Endothelial-derived IL-8 can also protect against leukocyte mediated damage to endothelial cells. This protection may occur because of the leukocyte adhesion inhibiting activity of endothelial-derived IL-8. However, other mechanisms separate from adhesion inhibiting activity may be involved. Therefore, the methods of the present invention are not bound by any disclosed mechanisms.

Before the present invention IL-8 was designated as a proinflammatory chemoattractant. No leukocyte adhesion inhibiting activity had been attributed to IL-8. Therefore, the present invention encompasses the use of IL-8 and related peptides from sources other than vascular endothelial cells, as anti-inflammatory agents and/or as therapeutics for clinical indications in which leukocyte mediated damage of vascular endothelium or other tissues occurs. Effective amounts of IL-8 to be administered in vivo can be determined by in vitro and in vivo bioassays as explained in more detail below.

The present invention relates to endothelial-derived IL-8 as well as to its functional derivatives. The invention additionally pertains to processes for preparing and purifying endothelial-derived IL-8, screening assays for endothelial-derived IL-8, diagnostic and therapeutic uses of endothelial-derived IL-8, and compositions containing endothelial-derived IL-8 or its functional derivatives.

In particular, the invention includes the leukocyte adhesion inhibitor endothelial-derived IL-8 or its functional derivatives, which are substantially free of natural contaminants. The invention further pertains to endothelial-derived IL-8 and its derivatives which are detectably labeled.

The invention also includes a method for recovering endothelial-derived IL-8 in substantially pure form which includes, but is not limited to the following steps:

(a) harvesting conditioned media from cell source;

(b) ultrafiltration of conditioned media to obtain endothelial-derived IL-8-containing fraction;

(c) concentration and desalting of endothelial-derived IL-8 by ultrafiltration;

(d) lyophilization and delipidation of endothelial-derived IL-8 by acetone precipitation;

(e) gel filtration of endothelial-derived IL-8 by HPLC-chromatography;

(f) ion exchange chromatography of endothelial-derived IL-8; and (g) recovering the filtrate obtained in step (f) in substantially pure form.

The invention includes the endothelial-derived IL-8 obtained by the above methods.

The invention is also directed to a method of treating inflammation in a mammalian subject which comprises providing to said subject in need of such treatment an amount of an anti-inflammatory agent sufficient to suppress said inflammation; wherein said anti-inflammatory is selected from the group consisting of: endothelial-derived IL-8, a fragment of endothelial-derived IL-8, a chemical derivative of endothelial-derived IL-8, a variant of endothelial-derived IL-8, and an analogue of endothelial-derived IL-8.

The invention also encompasses compositions and methods for protecting against leukocyte mediated damage to endothelial cells.

The invention also includes the above method for treating inflammation wherein said anti-inflammatory agent is administered in a suitable carrier. The invention also relates to a pharmaceutical composition for treating inflammation in a mammalian subject comprising administering an inflammation-reducing amount of an anti-inflammatory agent, wherein said agent is selected from the group consisting of: endothelial-derived IL-8, a fragment of endothelial-derived IL-8, a chemical derivative of endothelial-derived IL-8, a variant of endothelial-derived IL-8, and an analogue of endothelial-derived IL-8.

The invention is further directed to a method of diagnosing the presence and location of inflammation in a mammalian subject suspected of having an inflammation which comprises: (a) administering to said subject a composition containing a detectably labeled binding molecule (e.g., antibody) capable of binding and identifying endothelial-derived IL-8; and (b) detecting said binding molecule.

The invention also pertains to a method of diagnosing the presence and location of an inflammation in a mammalian subject suspected of having an inflammation which comprises: (a) incubating a biological sample from said subject suspected of containing endothelial-derived IL-8 in the presence of a detectably labeled binding molecule (e.g., antibody) capable of identifying endothelial-derived IL-8; and (b) detecting said binding molecule which is bound in said sample. Said biological sample may include a biopsy specimen or body fluid such as blood (serum or plasma), joint/pleural/peritoneal exudate, cerebral spinal fluid, or ocular fluid, for example.

The invention therefore includes novel methods for recovering and purifying the new endothelial-derived IL-8 molecule and its functional derivatives, diagnosing and treating inflammation in a mammalian subject, and novel compositions containing endothelial-derived IL-8 or its functional derivatives.

An understanding of this process of leukocyte adhesion inhibition, and of the endothelial-derived IL-8 molecule itself, will aid in the development of its therapeutic and/or diagnostic uses in such fields as rheumatology, organ transplantation, allergy and oncology. Additionally, endothelial-derived IL-8 may be useful in the treatment of adult respiratory distress syndrome, septic shock, vasculitis, ischemiareperfusion injury in the heart and other vital organs, and other inflammatory disease processes in which leukocyte (neutrophil) dependent injury to vascular-endothelium or other tissues occurs.

This invention will enable those in the medical field to more effectively diagnose and treat inflammatory disease processes, and to utilize a quantitative assay for endothelial-derived IL-8 in order to monitor the time-course and/or intensity of on-going clinical episodes of inflammation. The invention will further enable researchers to investigate the mechanisms of leukocyte-endothelial cell interactions and leukocyte function in inflammation.

(A) PMN ($2 \times 10^6$/ml) were resuspended in 1.9 ml HBSS was Ca$^{++}$ and Mg$^{++}$ (2 mill) and equilibrated with diSC$_3$-(5) (1.5 $\mu$M final conc.) at 37° C. in a SPEX fluorimeter. 100 $\mu$l aliquot of a 20x-concentrated SHAM CM (dotted line) or IL-1 CM (solid line) was added. After 5 min, $10^{-7}$M FMLP (top panel), $10^{-7}$M LTB$_4$ (middle panel), or 100 ng/ml PMA (bottom panel) was added and the increase in fluorescence recorded. F=10% full-scale.

(B) Fura-2-loaded PMN ($1 \times 10^6$/ml) were suspended in 1.9 ml HBSS with Ca$^{++}$ and Mg$^{++}$. 100 $\mu$l aliquot of 20x concentrated IL-1 CM (top) or SHAM CM (bottom) was added. After 5 min, $10^{-7}$M FMLP was added and the change in fluorescence emission (excitation 340 and 380) was recorded at 505 nm. Cytosolic free calcium concentrations (y axis) were calculated from the ratio of emitted fluorescence signals (see Grynkiewicz et al., *J. Biol. Chem.* 260:3440-3450 (1985)).

Figure 8:
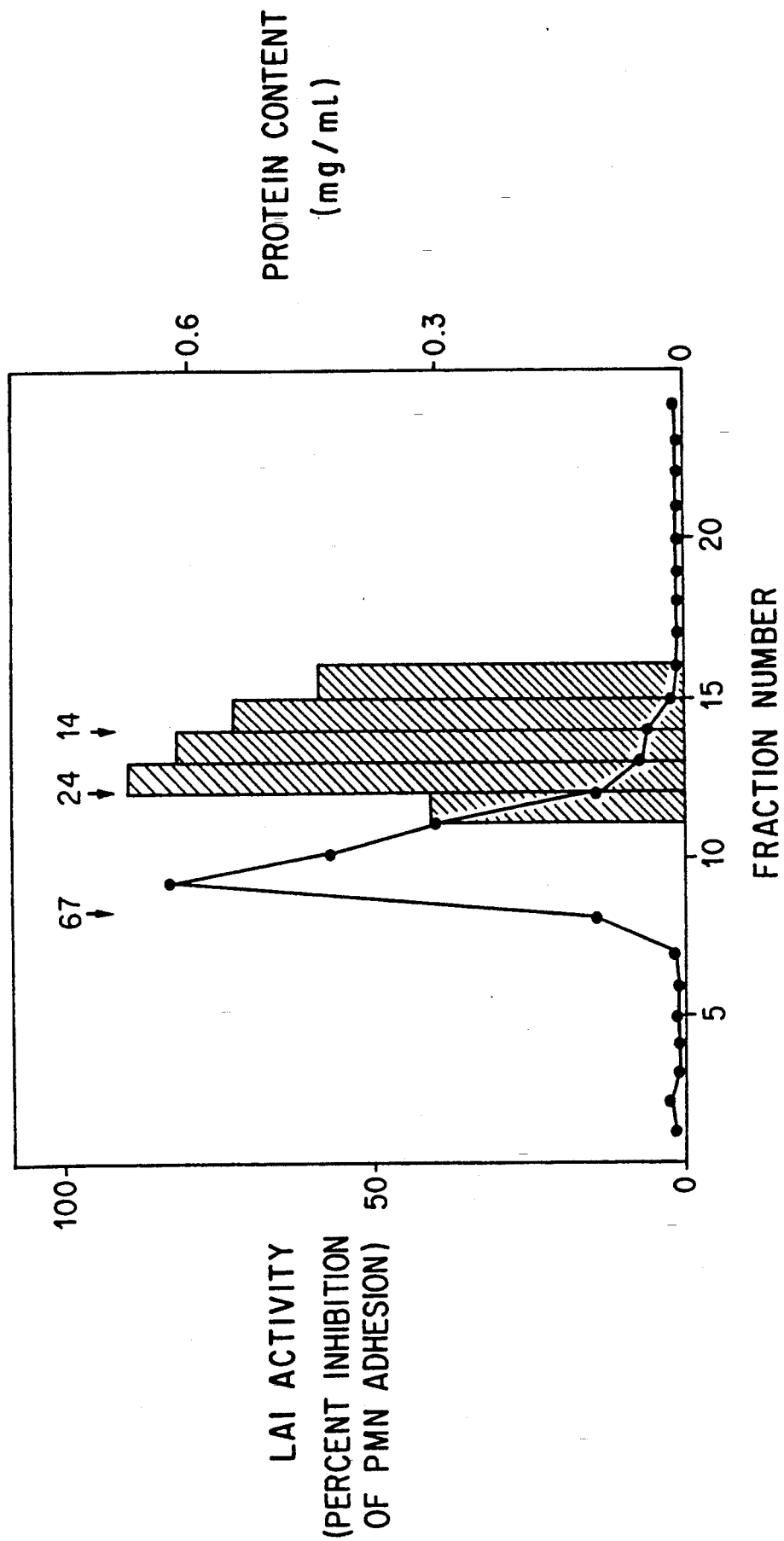

FIG. 8. Fractionation of IL-1 CM by high-pressure liquid chromatography is depicted. IL-LCM was collected in serum-free, TIS-supplemented medium, filtered through an Amicon YM 30 membrane, concentrated on a YM 5 membrane, washed to remove salts, and lyophilized. Aliquots were resuspended in 0.2M acetic acid, 0.1M triethylamine (pH 3.9), and applied to a Waters Protein-PAK 125 gel filtration column. Fractions were collected at a flow rate of 1.8 ml/min, dialyzed against PBS and diluted 1:10 with RPMI+FCS for assay of LAI activity (stippled bars). Protein content was determined in undiluted fractions in PBS (closed circles). Similar results were obtained in three additional experiments.

Figure 9:
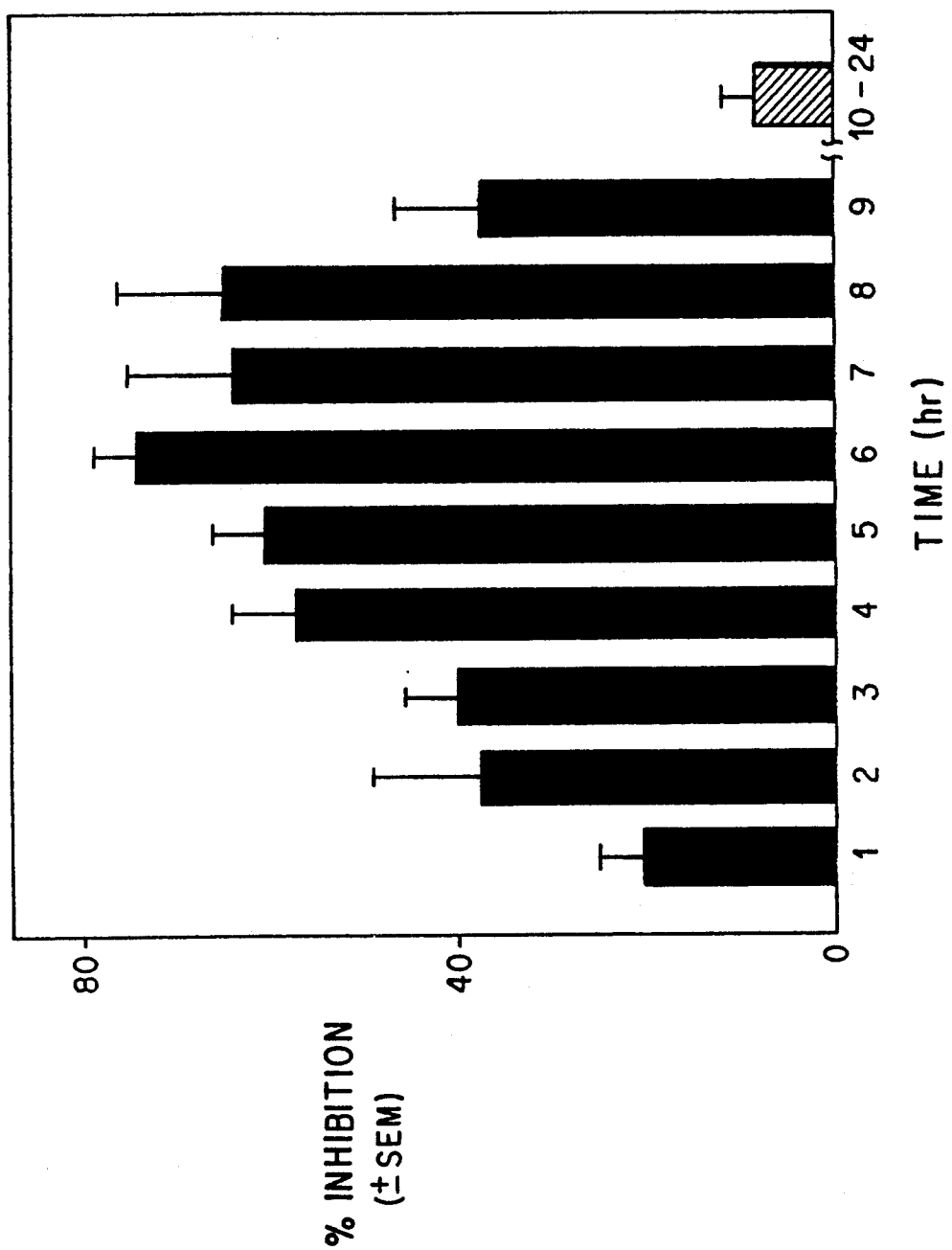

FIG. 9. Fractionated collection of LAI is depicted. The appearance of LAI, endothelial-derived IL-8, in the collection medium is time-dependent as determined by fractionated (hourly) collections. The HEC cultures were treated at time zero with 5 U/ml interleukin-1. At one hour, the medium was collected and replaced with fresh medium. Cytokine was added to the replacement medium until hour 5. As illustrated in this figure, endothelial-derived IL-8 was evident in the medium as early as 1 hour, reached peak production between 4 and 5 hours and was maintained until 9 hours. After 9 hours, a decline in activity was observed.

Figure 10:
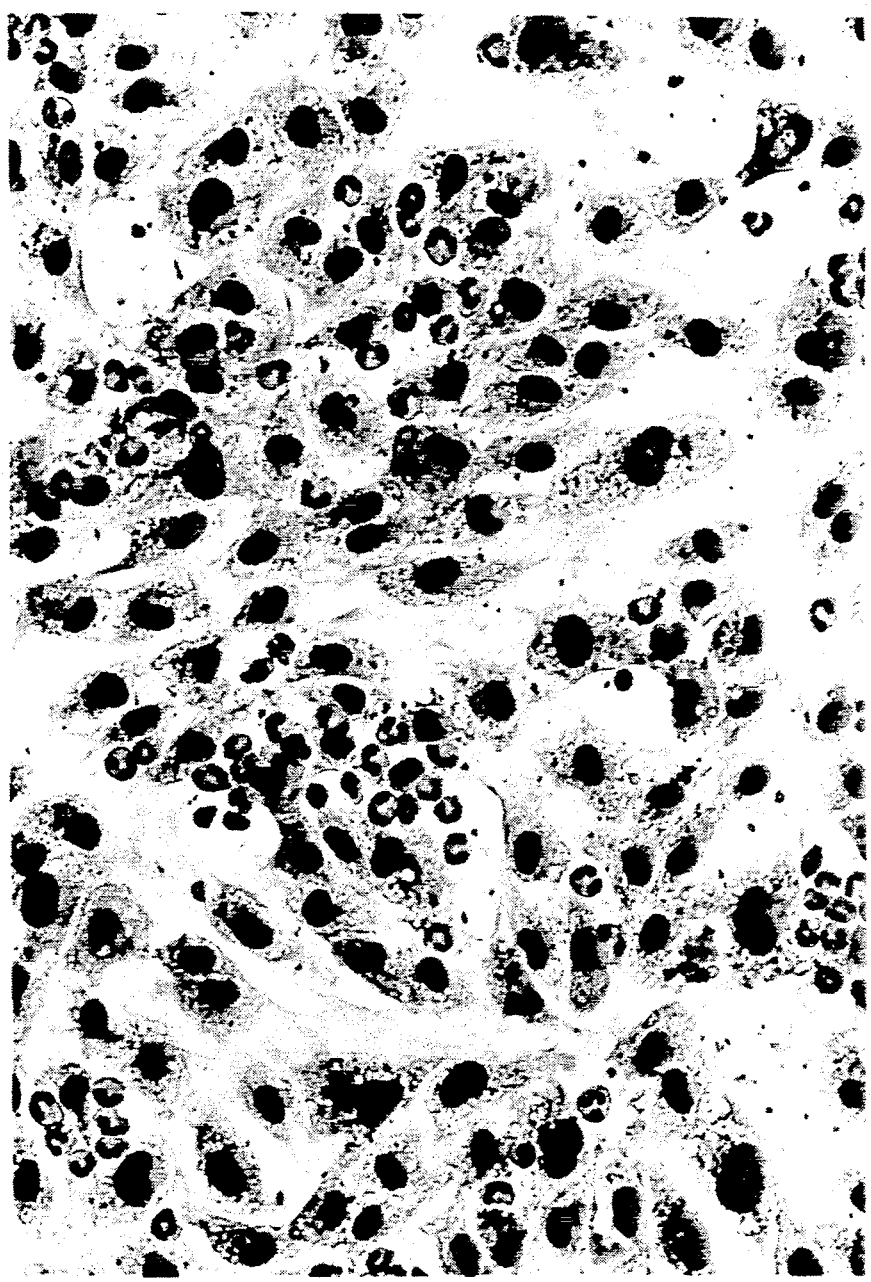
Figure 10B:
Figure 10C:
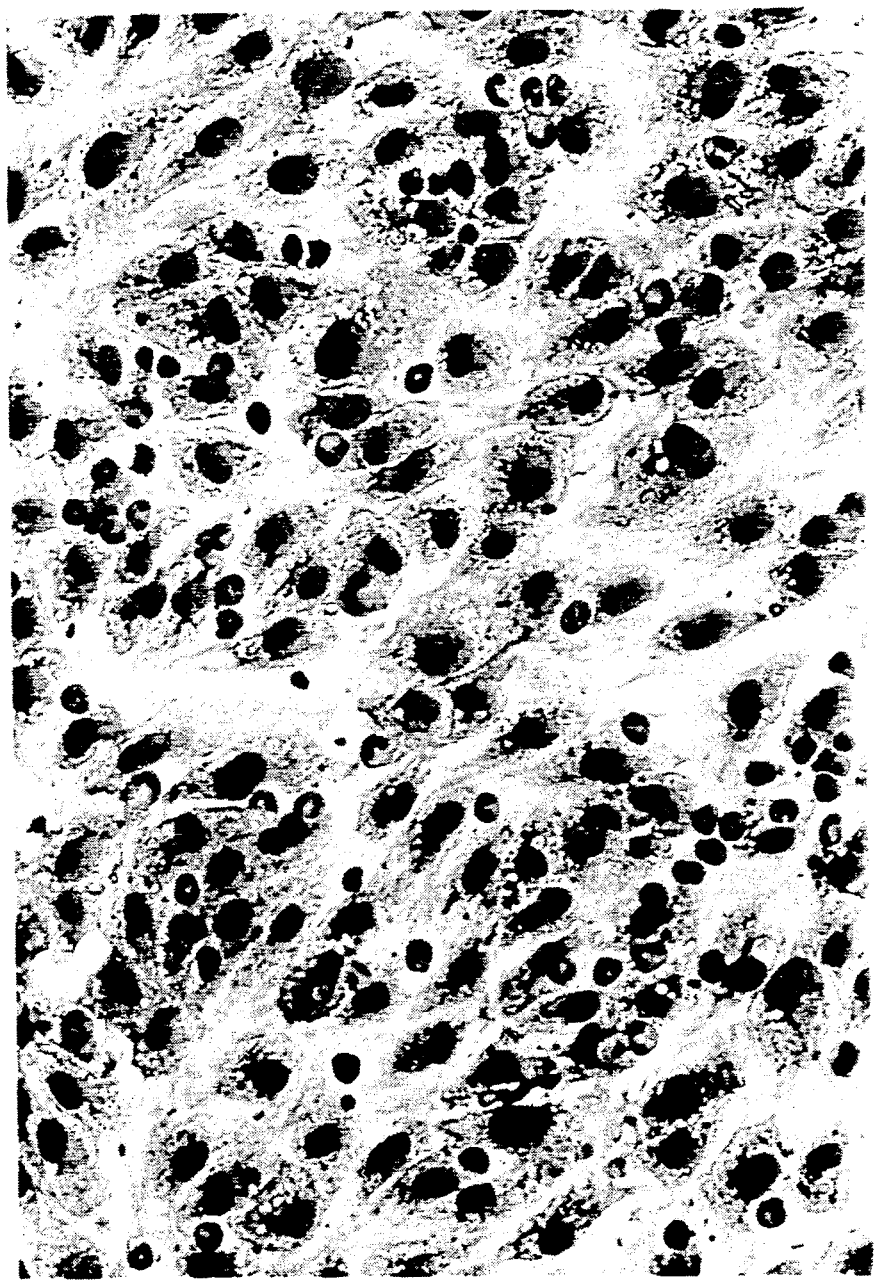

FIGS. 10(A-C). Protection of cytokine-activated endothelial monolayers from neutrophil-mediated injury by endothelial-derived LAI. Photomicrographs of HEC monolayers after 90-min incubation with neutrophils (50:1). (a) Unactivated HEC monolayer; (b) cytokine-activated HEC monolayer; note extensive monolayer retraction and cell loss; (c) cytokine-activated HEC monolayer in the presence of endothelial-derived LAI; note lack of damage manifested in (b).

DESCRIPTION OF THE PREFERRED EMBODIMENTS

One aspect of the present invention relates to the discovery of a natural intercellular adhesion inhibitor, referred to as endothelial-derived IL-8. The invention is directed toward substantially pure endothelial-derived IL-8. Substantially pure endothelial IL-8 includes a mixture of IL-8 molecules. The mixture comprises [Ala IL-8]$_{77}$ as the predominant polypeptide with [Ser IL-8]$_{72}$ as a minor component. Generally, [Ala IL-8]$_{77}$ will comprise from about 70% to about 95% of the mixture. [Ala IL-8]$_{77}$ and a biochemical method for its separation from [Ser IL-8]$_{72}$ are described and claimed in copending U.S. application Ser. No. 07/443,131, filed Nov. 29, 1989, now abandoned.

The term "functional derivatives" is intended to include the "fragments," "variants," "analogues," or "chemical derivatives" of the subject polypeptides. A "fragment" of endothelial-derived IL-8 polypeptides is meant to refer to polypeptide subsets. A "variant" of the polypeptides is meant to refer to a naturally occurring molecules substantially similar to either the entire molecules, or fragments thereof. An "analogue" of endothelial-derived IL-8 is meant to refer to a non-natural molecule substantially similar to either the entire molecules or fragments thereof. A molecule is said to be "substantially similar" to another molecule if the sequence of amino acids in both molecules is substantially the same, and if both molecules possess a similar biological activity. Thus, provided that two molecules possess a similar activity, they are considered variants as that term is used herein even if one of the molecules contains additional amino acid residues not found in the other, or if the sequence of amino acid residues is not identical.

As used herein, a molecule is said to be a "chemical derivative" of another molecule when it contains additional chemical moieties not normally a part of the molecule. Such moieties may improve the molecule's solubility, absorption, biological half-life, etc. The moieties may alternatively decrease the toxicity of the molecule, eliminate or attenuate any undesirable side effect of the molecule, etc. Examples of moieties capable of mediating such effects are disclosed in *Remington's Pharmaceutical Sciences* (1980) and will be apparent to those of ordinary skill in the art.

A suitable screening method for determining whether a given compound is an endothelial-derived IL-8 functional derivative comprises, for example, bioassays as described for PMN-endothelial cell adhesion as well as immunoassay, employing RIA or ELISA methodologies, based on the production of specific neutralizing antibodies (monoclonal or polyclonal) to natural endothelial-derived IL-8.

Endothelial-derived IL-8 disclosed herein is said to be "substantially free of natural contaminants" if preparations which contain it are substantially free of materials with which this product is normally and naturally found. However, as indicated earlier, substantially pure endothelial-derived IL-8 is a mixture comprising [Ala IL-8]$_{77}$ and [Ser IL-8]$_{72}$ polypeptides. While the methods of the present invention are able to separate this mixture from natural contaminants, the present methods, or others known in the art, are not able to separate the two components.

For purposes of the present invention, preferred methods of purification include generating rabbit heterosera and mouse monoclonal antibodies for use in immunoaffinity chromatography purification, ion-exchange chromatography on a cation exchange column such as Mono S, and preparative SDS-PAGE followed by electroelution. For purposes of example, and without being limiting, a preferred method of purification includes the following steps and materials:

a) endothelial-derived IL-8 is collected from cell source in RPMI-1640 (M.A. Bioproducts) supplemented with ITS (Collaborative Research, Bedford, Mass.).

b) Media is ultrafiltered on Amicon-stirred ultrafiltration cell using membrane YM-30.

c) Media from step (b) is concentrated on YM-5, washed to desalt with Milli-Q purified water (Millipore), frozen and lyophilized. Contaminating lipid is removed by washing the lyophilized pellet with five volumes ice-cold acetone.

d) Lyophilized material is reconstituted in 0.2M acetic acid (Fisher Scientific) and 0.1M triethylamine (Sigma Chemical Co.) and applied to a Protein-Pak 125 gel filtration column (Waters).

e) Fractions from (d) are dialyzed into 10 mM Tris pH 7 (BioRad) and incubated for 20 min at 25° C. with CM-sephadex or SP-sephadex (Pharmacia) equilibrated in 10 mM Tris pH 7. endothelial-derived IL-8 activity is removed by both cation exchange resins.

One may also employ a citrate-based buffer system. Elution of activity is accomplished with a linear salt gradient (0.01M to 1M NaCl). Fractions from this procedure may be tested for endothelial-derived IL-8 activity and subjected to SDS polyacrylamide gel electrophoresis.

Also contemplated by the present invention are purified endothelial-derived IL-8 fragments or its derivatives manufactured using organic synthesis or recombinant DNA techniques, or by proteolysis.

The present invention also includes methods of detecting endothelial-derived IL-8 or functional derivatives in a sample or subject. For example, antibodies specific for endothelial-derived IL-8, or functional derivatives thereof, may be detectably labeled with any appropriate ligand, for example, a radioisotope, an enzyme, a fluorescent label, a paramagnetic label, or a free radical. The presence of inflammation may be detected through the use of such detectably labeled materials. Methods of making and detecting such detectably labeled antibodies or their functional derivatives are well known to those of ordinary skill in the art.

The detection of foci of such detectably labeled antibodies is indicative of a site of inflammation. In one embodiment, this examination for inflammation is accomplished by removing samples of tissue or blood and incubating such samples in the presence of detectably labeled antibodies. In a preferred embodiment, this technique is accomplished in a non-invasive manner through the use of magnetic imaging, fluorography, etc. For example, such a diagnostic test may be employed in monitoring organ transplant recipients for early signs of potential tissue rejection. Such assays may also be conducted in efforts to determine a subject's clinical status in rheumatoid arthritis and other chronic inflammatory diseases.

It is possible to use antibodies, or their functional derivatives, to detect or diagnose the presence and location of an inflammation in a mammalian subject suspected of having an inflammation by utilizing an assay for endothelial-derived IL-8, comprising incubating a biological sample from said subject suspected of containing endothelial-derived IL-8 in the presence of a detectably labeled binding molecule (e.g., antibody) capable of identifying endothelial-derived IL-8, and detecting said binding molecule which is bound in a sample.

Thus, in this aspect of the invention, a biological sample may be treated with nitrocellulose, or other solid support which is capable of immobilizing cells, cell particles or soluble protein. The support may then be washed with suitable buffers followed by treatment with the detectably labeled endothelial-derived IL-8-specific antibody. The solid phase support may then be washed with the buffer a second time to remove unbound antibody. The amount of bound label on the antibody may then be detected by conventional means.

In carrying out the assay of the present invention on a sample containing endothelial-derived IL-8, the process comprises:

(a) contacting a sample suspected containing endothelial-derived IL-8 with a solid support to effect immobilization of endothelial-derived IL-8;

(b) contacting said solid support with a detectably labeled endothelial-derived IL-8-specific antibody;

(c) incubating said detectably labeled endothelial-derived IL-8-specific antibody with said support for a time sufficient to allow the endothelial-derived IL-8-specific antibody to bind to the immobilized endothelial-derived IL-8;

(d) separating the solid phase support from the incubation mixture obtained in step (c); and (e) detecting the bound label and thereby detecting and quantifying endothelial-derived IL-8.

This aspect of the invention relates to a method for detecting endothelial-derived IL-8 or fragment thereof in a sample comprising (a) contacting a sample suspected of containing endothelial-derived IL-8 with an endothelial-derived IL-8-specific antibody or fragment thereof which binds to endothelial-derived IL-8; and (b) detecting whether a complex is formed.

Of course, the specific concentrations of detectably labeled antibody and endothelial-derived IL-8, the temperature and time of incubation, as well as other assay conditions may be varied, depending on various factors including the concentration of endothelial-derived IL-8 in the sample, the nature of the sample, and the like. Those skilled in the art will be able to determine operative and optimal assay conditions for each determination by employing routine experimentation.

Other such steps as washing, stirring, shaking, filtering and the like may be added to the assays as is customary or necessary for the particular situation.

One of the ways in which the endothelial-derived IL-8-specific antibody can be detectably labeled is by linking the same to an enzyme. This enzyme, in turn, when later exposed to its substrate, will react with the substrate in such a manner as to produce a chemical moiety which can be detected, for example, by spectrophotometric, fluorometric or by visual means. Enzymes which can be used to detectably label the endothelial-derived IL-8-specific antibody include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase.

The endothelial-derived IL-8-specific antibody may also be labeled with a radioactive isotope which can be determined by such means as the use of a gamma counter or a scintillation counter or by audioradiography. Isotopes which are particularly useful for the purpose of the present invention are: $^3H$, $^{125}I$, $^{131}I$, $^{35}S$, $^{14}C$, and $^{51}Cr$.

It is also possible to label the endothelial-derived IL-8-specific antibody with a fluorescent compound. When the fluorescently labeled antibody is exposed to light of the proper wave length, its presence can then be detected due to the fluorescence of the dye. Among the most commonly used fluorescent labelling compounds are fluorescein isothiocyanate, rhodamine, phycoerytherin, phycocyanin, allophycocyanin, o-phthaldehyde and fluorescamine.

The endothelial-derived IL-8-specific antibody can also be detectably labeled using fluorescence emitting metals such as $^{152}Eu$, or others of the lanthanide series. These metals can be attached to the endothelial-derived IL-8-specific antibody using such metal chelating groups as diethylenetriaminepentaacetic acid (DTPA) or ethylenediaminetetraacetic acid (EDTA).

The endothelial-derived IL-8-specific antibody also can be detectably labeled by coupling it to a chemiluminescent compound. The presence of the chemiluminescent-tagged endothelial-derived IL-8-specific antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the endothelial-derived IL-8-specific antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Detection of the endothelial-derived IL-8-specific antibody may be accomplished by a scintillation counter, for example, if the detectable label is a radioactive gamma emitter, or by a fluorometer, for example, if the label is a fluorescent material. In the case of an enzyme label, the detection can be accomplished by colorimetric methods which employ a substrate for the enzyme. Detection may also be accomplished by visual comparison of the extent of enzymatic reaction of a substrate in comparison with similarly prepared standards.

Endothelial-derived IL-8 is a soluble product of the activated endothelial cell and, as such, is involved in inflammatory processes. The term "inflammation" is meant to include reactions of both the specific and nonspecific defense systems. A specific defense system reaction is a specific immune system reaction response to an antigen. Examples of a specific defense system reaction include the antibody response to antigens such as rubella virus, and delayed-type hypersensitivity response mediated by T-cells (as seen, for example, in individuals who test "positive" in the Mantaux test).

A non-specific defense system reaction is an inflammatory response mediated by leukocytes incapable of immunological memory. Such cells include granulocytes, macrophages, neutrophils, etc. Examples of a non-specific defense system reaction include the immediate swelling at the site of a bee sting, the reddening and cellular infiltrate induced at the site of a burn, and the collection of PMN leukocytes at sites of bacterial infection (e.g., pulmonary infiltrates in bacterial pneumonias, pus formation in abscesses).

It will be appreciated that the present invention will be easily adapted to the diagnosis, monitoring, and treatment of inflammatory disease processes such as rheumatoid arthritis, acute and chronic inflammation, post-ischemic (reperfusion) leukocyte-mediated tissue damage, acute leukocyte-mediated lung injury (e.g., Adult Respiratory Distress Syndrome), and other tissue- or organ-specific forms of acute inflammation (e.g., glomerulonephritis).

As would be apparent to one of ordinary skill in the art, the therapeutic effects of endothelial-derived IL-8 may be obtained by providing to a patient the entire endothelial-derived IL-8 molecules, or any therapeutically active peptide fragments thereof.

As is also apparent, the therapeutic advantages of endothelial-derived IL-8 may be augmented through the use of endothelial-derived IL-8 mutants or variants possessing additional amino acid residues added to enhance its coupling to a carrier or to enhance the activity of endothelial-derived IL-8. The scope of the present invention is further intended to include mutant forms of endothelial-derived IL-8 (including endothelial-derived IL-8 molecules which lack certain amino acid residues, or which contain altered amino acid residues, so long as such mutant endothelial-derived IL-8 molecules exhibit the capacity to affect cellular adhesion).

The endothelial-derived IL-8 polypeptides of the present invention and functional derivatives can be formulated according to known methods of preparing pharmaceutically useful compositions, whereby these materials or their functional derivatives are combined in a mixture with a pharmaceutically acceptable carrier vehicle. Suitable vehicles and their formulation, including other human proteins, e.g., human serum albumin, are described, for example, in *Remington's Pharmaceutical Sciences* (16th ed., Osol, A., Ed., Mack, Easton, Pa. (1980)). In order to form a pharmaceutically acceptable composition suitable for effective administration, such compositions will contain a therapeutically effective amount of endothelial-derived IL-8, or functional derivatives (an inflammation-reducing amount, protecting amount or leukocyte adhesion inhibiting amount), together with a suitable amount of carrier vehicle.

A preferred product of the invention is a sterile pharmaceutical composition for therapeutic use containing endothelial-derived IL-8 or its functional derivatives, which is suitable for intravenous administration. The product may be in lyophilized form to be reconstituted for use by addition of a suitable carrier, or diluent, or it may be in the form of an aqueous solution.

For reconstitution of a lyophilized product in accordance with this invention, one may employ a sterile diluent, which may contain materials generally recognized for approximating physiological conditions and/or as required by governmental regulation. In this respect, the sterile diluent may contain a buffering agent to obtain a physiologically acceptable pH, such as sodium chloride, saline, phosphate-buffered saline, and/or other substances which are physiologically acceptable and/or safe for use. In general, the material for intravenous injection in humans should conform to regulations established by the Food and Drug Administration, which are available to those in the field.

The pharmaceutical composition may also be in the form of an aqueous solution containing many of the same substances as described above for the reconstitution of a lyophilized product.

As mentioned above, the products of the invention may be incorporated into pharmaceutical preparations which may be used for therapeutic purposes. However, the term "pharmaceutical preparation" is intended in a broader sense herein to include preparations containing a protein composition in accordance with this invention, used not only for therapeutic purposes but also for reagent or diagnostic purposes as known in the art, or for tissue culture. The pharmaceutical preparation intended for therapeutic use should contain a "pharmaceutically acceptable" or "therapeutically effective amount" of endothelial-derived IL-8, i.e., that amount necessary for preventative or curative health measures. If the pharmaceutical preparation is to be employed as a reagent or diagnostic, then it should contain reagent or diagnostic amounts of endothelial-derived IL-8.

By definition, one unit of endothelial-derived IL-8 activity will produce 50% inhibition of PMN adhesion at a PMN concentration of $2 \times 10^6$ cells/ml in a standardized in vitro assay system. A ten-fold higher concentration of endothelial-derived IL-8 (10 U/ml) produces a maximal inhibition of 85–90%.

The therapeutic and/or diagnostic dosage administered in vivo will be dependent upon the particular inflammatory condition involved and may be dependent upon the age, weight, height, sex, general medical condition, and kind of concurrent treatment, if any, of the mammalian subject. In general, it is desirable to provide the recipient with a dosage which is sufficient to obtain an effective concentration of greater than about 10 U/ml of endothelial IL-8 activity, although a lower or higher dosage may be administered. The specific activity of a given preparation of endothelial-derived IL-8, or derivatives thereof, can be determined by an in vitro bioassay, as set forth below in the Experimental Section. In this manner, the dosage for any preparation of endothelial-derived IL-8, or derivatives, may be determined.

Methods useful for administering the molecules of the present invention include topical, subcutaneous, intravenous, intraarterial, intraarticular, intraperitoneal, intrapleural, or intraocular. When administering endothelial-derived IL-8 or its functional derivatives by injection, the administration may be by continuous infusion, or by single or multiple boluses.

The effective molecule useful in the methods of the present invention may be employed in such forms as, for example, sterile suspensions for injection or encapsulated for targeting to specific tissue sites with antibodies directed to inflammation-related cell surface structures such as ELAM-1 (Bevilacqua et al., *PNAS U.S.A.* 84:9238–9242 (1987); Cotran et al., *J. Exp. Med.* 164:661–666 (1986)).

Additional pharmaceutical methods may be employed to control the duration of action. Controlled release preparations may be achieved through the use of polymers to complex or absorb endothelial-derived IL-8 or its functional derivatives. The controlled delivery may be achieved by selecting appropriate macromolecules (for example, polyesters, polyamino acids, polyvinyl, pyrrolidone, ethylenevinylacetate, methylcellulose, carboxymethylcellulose, or protamine, sulfate) and the appropriate concentration of macromolecules as well as the methods of incorporation, in order to control release.

Another possible method useful in controlling the duration of action by controlled release preparations is incorporation of the endothelial-derived IL-8 molecule or its functional derivatives into particles of a polymeric material such as polyesters, polyamino acids, hydrogels, poly(lactic acid), or ethylene vinylacetate copolymers. Alternatively, instead of incorporating endothelial-derived IL-8 or its functional derivatives into polymeric particles, it is possible to entrap these materials in microcapsules prepared, for example, by coacervation techniques or by interfacial polymerization (for example, hydroxymethylcellulose or gelatine-microcapsules and poly-(methylmethacylate) microcapsules, respectively), in colloidal drug delivery systems (for example, liposomes, albumin microspheres, microemulsions, nanoparticles, and nanocapsules), or in macroemulsions. Such techniques are disclosed in *Remington's Pharmaceutical Sciences* (1980).

EXAMPLES

Having now fully described the present invention, the same will be more clearly understood by reference to certain specific examples which are included herewith for purposes of illustration only and are not intended to be limiting of the invention, unless specified.

Inflammatory Materials and Biochemical Reagents

The following reagents were obtained from the sources indicated. Human monocyte derived IL-1 (hmIL-1), human recombinant IL-1-$\beta$ (rIL-1$\beta$), and human recombinant granulocytemonocyte colony stimulating factor (GM-CSF): Genzyme, Inc., Boston, Mass.; human recombinant IL-1-$\alpha$ (rIL-1$\alpha$) expressed in *E. coli*: Cistron Technology, Pine Brook, N.J.; Gram-negative bacterial endotoxin (*E. coli* 0111:B4): Difco Laboratories, Detroit, Mich.; affinity-purified human interferon gamma ($\gamma$-IFN): Interferon Sciences, Inc., New Brunswick, N.J.; trypsin (Type XI), thrombin (from human plasma), N-formyl-methionyl-leucyl-phenylalanine (fMLP), phorbol 12-myristate 13-acetate (PMA), gelatin-agarose, and ammonium sulphate (Grade III): Sigma Chemical Co., St. Louis, Mo.; leukotriene B$_4$ (LTB$_4$): Biomol, Inc., Philadelphia, Pa.; concanavalin A-agarose: Vector Laboratories, Burlingame, Calif.; heparin-sepharose CL-6B and pepsin-agarose: Pharmacia, Uppsala, Sweden. Heparinase from *Flavobacterium heparinium* was provided by Dr. Howard Bernstein (Massachusetts Institute of Technology, Cambridge, Mass.). Recombinant TNF (rTNF), rIL-2, and rIL-1$\beta$ were provided by Biogen, Inc. (Cambridge, Mass.).

In the following examples endothelial-derived IL-8 is sometimes referred to as LAI (leukocyte adhesion inhibitor).

Example 1

Cell Cultures

Human umbilical vein endothelial cells (HEC) were isolated and passaged from two to five cord segments, pooled, and grown in primary culture using Medium 199 (M199, M.A. Bioproducts, Bethesda, Md.), with 20% fetal calf serum (FCS, Gibco Laboratories, Grand Island, N.Y.) and antibiotics as previously described (Bevilacqua et al., *J. Clin. Invest.* 76:2003-2011 (1985)). Several strains were serially passaged (1:3 split ratios) using M199-20% FCS supplemented with endothelial cell growth factor (50-100 $\mu$g/ml; Biomedical Technologies, Inc., Stoughton, Mass.) and porcine intestinal heparin (50-100 $\mu$g/ml; Sigma Chemical Co., St. Louis, Mo.) in Costar tissue culture flasks (75 cm$^2$, Costar, Cambridge, Mass.) coated with 0.1% gelatin (Bactogelatin 0143-02, Difco Laboratories, Detroit, Mich.).

For experimental use, HEC strains were plated (passage levels 2-5) on 15 mm Thermanox plastic coverslips (Miles Scientific, Naperville, Ill.), in microtiter wells, or 100 mm tissue-culture dishes (Corning Glass Works, Corning, N.Y.) coated with either fibronectin (1 $\mu$g/cm$^2$, Meloy Laboratories, Springfield, Va.) or 0.1% gelatin.

Example 2

Isolation and Radiolabeling of Leukocytes

Blood was drawn from normal human volunteers into CCD buffer (1:9; 100 mM sodium citrate, 130 mM glucose, pH 6.5). Suspensions of PMN (>95%) were prepared according to the methods of Bevilacqua et al., *J. Clin. Invest.* 76:2003-2011 (1985). Mononuclear leukocytes were isolated on lymphocyte separation media (Litton Bionetics, Inc., Charleston, S.C.) and further fractionated into either a monocyte-enriched population (75-88%) according to the method of Recalde et al., *J. Immunol. Meth.* 69:71-77 (1984) or lymphocyte suspensions (>95%) by monocyte depletion on serum-coated plastic Petri dishes. The promyelocytic cell line HL-60 and the monocyte-like cell line U937 were cultured as described in Bevilacqua et al., supra. Each leukocyte type was radiolabeled with $^{111}$Indium-oxine (Amersham Corp., Arlington Heights, Ill.) using the techniques described by Bevilacqua et al., supra.

Example 3

Preparation of Medium

In order to prepare IL-1-conditioned medium (IL-1 CM) or sham-conditioned medium (SHAM CM), confluent HEC monolayers (100 mm dishes) were incubated with or without IL-1 (2.5-5 U/ml hmIL-1 or RIL-$\beta$) in RPMI-1640 (RPMI, M.A. Bioproducts, Walkersville, Md.) which contained the following: (1) no additional protein; (2) a defined non-serum additive containing 5 $\mu$g/ml transferrin, 5 $\mu$g/ml insulin, and 5 ng/ml selenium (final concentration) (TIS; Collaborative Research, Cambridge, Mass.); (3) 1% (v/v) fetal calf serum (FCS, endotoxin <0.027 ng/ml, Hyclone Laboratories Inc., Logan, Utah); and (4) 10 mg/ml bovine serum albumin (BSA, Fraction V, Sigma Chemical Co.). After 4 h, all dishes were washed with 5 ml Hanks balanced salt solution (HBSS, M.A. Bioproducts) without Ca$^{++}$ or Mg$^{++}$ to remove the cytokine-containing medium and incubated for an additional 5 h in RPMI alone or supplemented with TIS, FCS, or BSA. Media were collected, centrifuged (400 x g, 10 min), and usually frozen at $-80°$ C.

In certain experiments, actinomycin D (5 $\mu$g/ml, Sigma Chemical Co.), acetylsalicylic acid (500 $\mu$M, Fisher Scientific Co., Medford, Mass.), or indomethacin (5 $\mu$M, Sigma Chemical Co.) were added to the endothelial cultures 30 min prior to the addition of rIL-1 and allowed to remain in the medium throughout the pretreatment phase.

Example 4

Enzymatic Treatment of LAI

LAI was treated enzymatically as follows: SHAM CM and IL-1 CM collected in RPMI+TIS were filtered through an Amicon YM 30 membrane (nominal molecular weight cut-off 30,000; Amicon Corp., Denvers, Mass.) under $N_2$ and treated with trypsin (1,000 U/ml, pH 7, 37° C., 18 h), thrombin (2 U/ml, 37° C., 2 h), heparinase (15 U/ml, 30° C., 2 h), or pepsin-linked agarose (4,500 U/ml, pH 4, 18 h, 37° C.). Enzyme treatments were stopped by boiling (15 min, 100° C.) or, in the case of pepsin-linked agarose, by centrifugation in a Beckman Microfuge with removal of the agarose beads. Trypsin and thrombin retained full activity in both SHAM CM and IL-1 CM as determined by the hydrolysis of chromagenic substrate BAEE (N-α-benzoyl-L-arginine ethyl ester; Sigma Chemical Co.) and plasma clotting activity, respectively.

Example 5

Assay of LAI Activity

LAI activity was assayed in a standard radiometric monolayer adhesion assay (see Bevilacqua et al., *J. Clin. Invest.* 76:2003–2011 (1985)). In brief, target monolayers consisting of confluent HEC monolayers, grown on Thermanox coverslips or in microtiter wells, were pretreated in RPMI+FCS with and without rIL-1β (2.5–5 U/ml, 4 h). Aliquots of $^{111}$Indium-labeled leukocyte suspensions ($2 \times 10^7$ cells/ml) were diluted directly in IL-1 CM, SHAM CM, or fresh RPMI+FCS or TIS (final concentration=$2 \times 10^6$ cells/ml), added to washed monolayers, and incubated at 37° C. for 10 min under static conditions. The assay was terminated by a standardized wash for HEC monolayers on Thermanox coverslips (see Bevilacqua et al., supra) or sealed, inverted, and centrifuged in the case of the microtiter plates (see Bevilacqua et al., *Prot. Natl. Acad. Sci. U.S.A.* 84:9238–9242 (1987); Charo et al., *Blood* 65:473–479 (1985)).

The number of adherent $^{111}$In-labeled leukocytes was determined from the monolayer-bound radioactivity and the specific activity (cpm/cell) of the leukocyte preparation using a Gamma 5500 counter (Beckman Instruments, Inc., Fullerton, Calif.). Percent inhibition was calculated as:

$$1 - \frac{\text{\# cells adherent/mm}^2 \text{ in } IL\text{-}1\ CM}{\text{\# cells adherent/mm}^2 \text{ in } SHAM\ CM} \times 100$$

and expressed as mean +/− standard error of the mean (SEM). Significance was tested with a two-tailed Student's T-test.

Example 6

Cytokine-Induced Increase in Adhesiveness of Endothelial Cells for PMN

Figure 1:
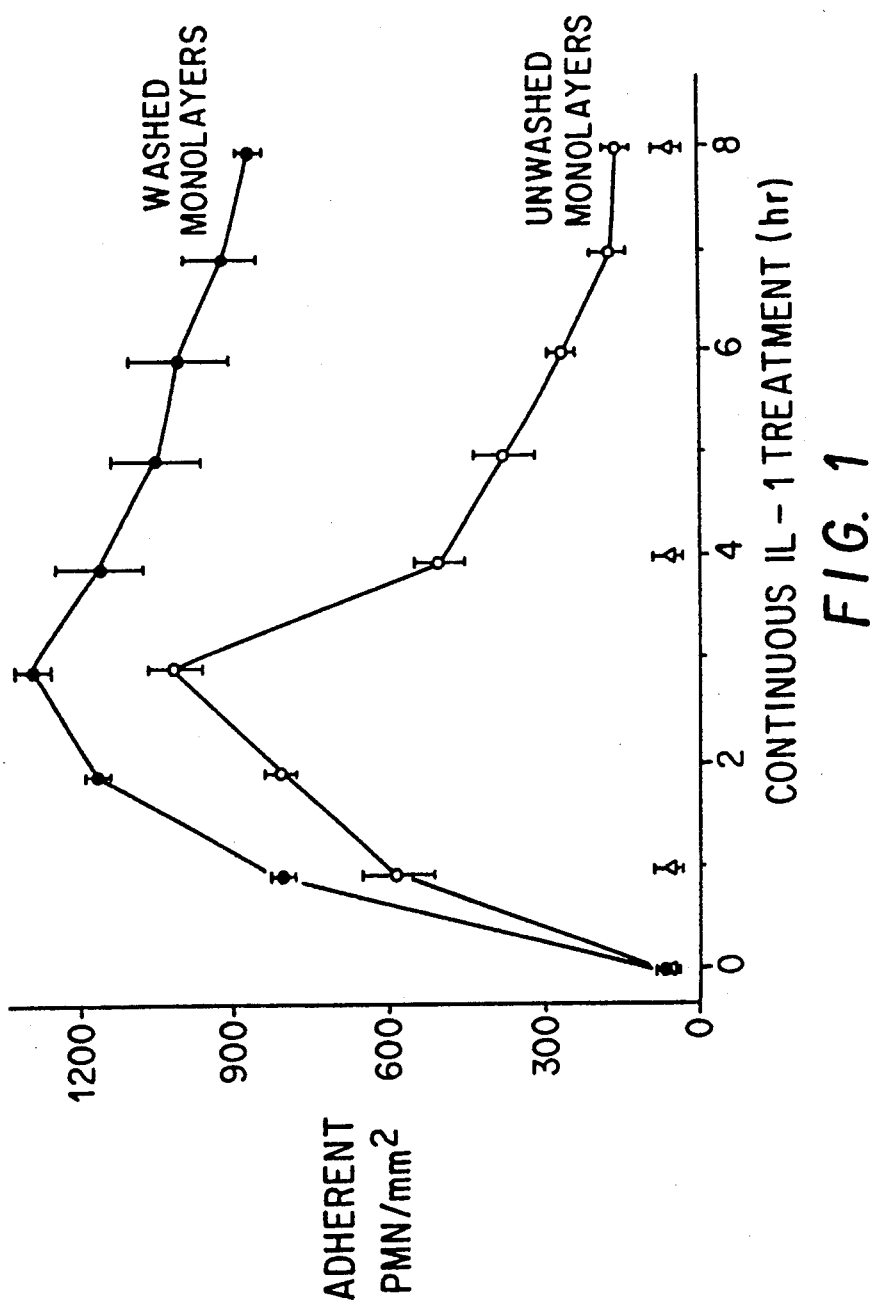
FIG. 1: PMN adhesion to IL-1-treated endothelial monolayers is depicted. $^{111}$Indium-labeled PMN were added to HEC monolayers pretreated with hmIL-1 (5 U/ml) for the times indicated, and the number of adherent PMN were determined in a standard 10-minute monolayer adhesion assay. Closed circles ("washed") indicate wells from which the conditioned medium was removed and the monolayers washed immediately prior to PMN addition. Open circles ("unwashed") indicate wells in which PMN were added directly into the conditioned medium. PMN adhesion to untreated HEC in the presence (open triangles) or absence (closed triangles) of conditioned medium is indicated at 1, 4, and 8 h.

As illustrated in FIG. 1, treatment of HEC monolayers with hmIL-1 resulted in a time-dependent increase in surface adhesiveness for polymorphonuclear leukocytes (PMN). In our standard monolayer adhesion assays (see Bevilacqua et al., *J. Clin. Invest.* 76:2003–2011 (1985)), the cytokine-containing medium routinely was aspirated and each well washed with fresh medium immediately prior to the addition of radiolabeled leukocytes. In this "washed" system, PMN adhesion to IL-1-treated HEC monolayers was significantly increased with respect to untreated monolayers as early as 1 h post-IL-1, with peak adhesion occurring between 3 and 4 h, followed by a gradual decline. In contrast, when the pretreatment media was not removed and PMN were added directly to the well ("unwashed" system), markedly less PMN adhesion was observed, especially after 3 h. PMN adhesion to unstimulated HEC monolayers was the same for both washed and unwashed conditions at all time points examined. Based on these observations, we hypothesized that the conditioned media from IL-1-stimulated, but not -unstimulated, HEC monolayers contained an activity which inhibits PMN-endothelial adhesion ("leukocyte adhesion inhibitor," LAI).

Example 7

Identification and Metabolic Evaluation of LAI Activity

Figure 2:
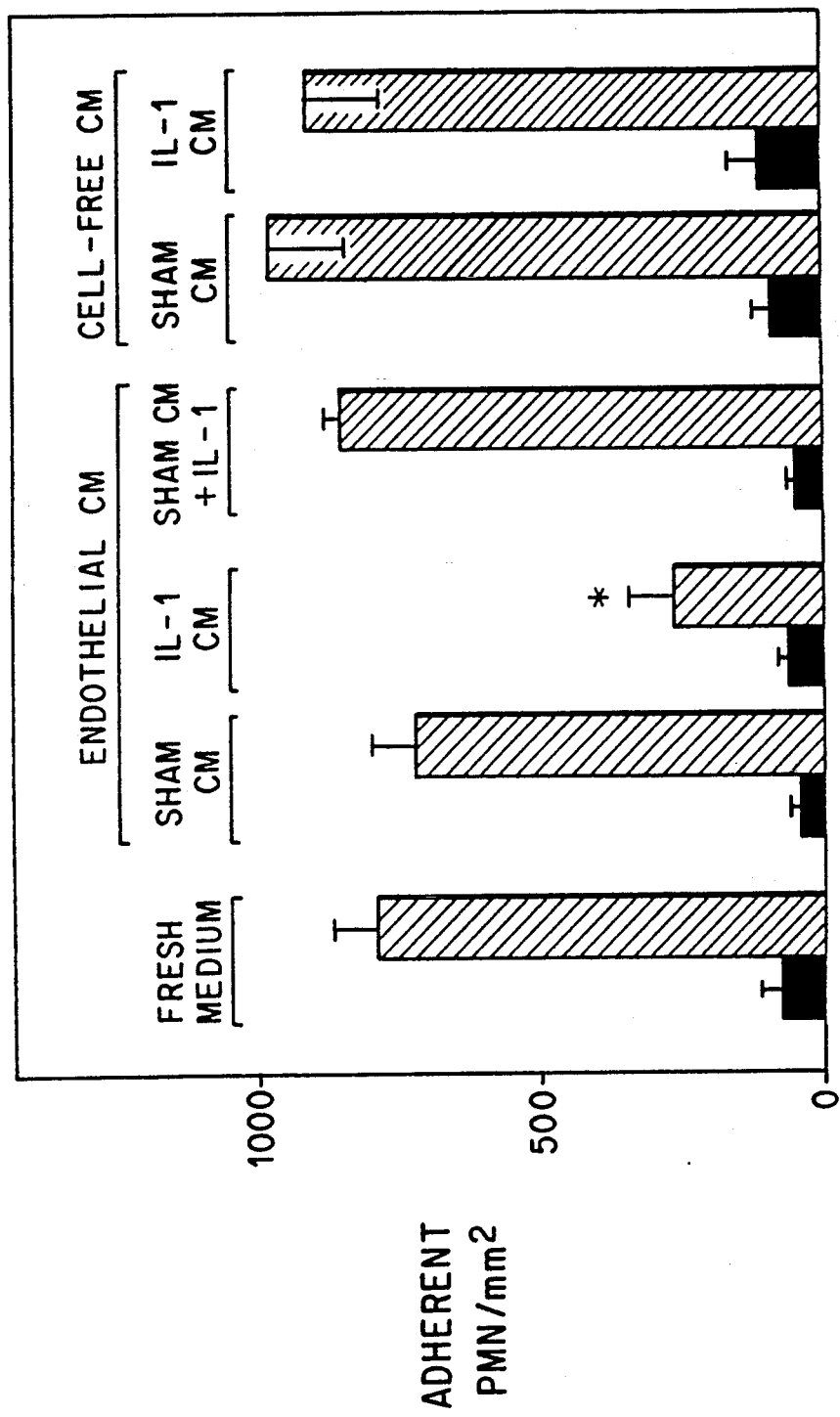
FIG. 2: Effect of various conditioned media on PMN adhesion to stimulated and unstimulated endothelial cells is depicted. Conditioned media were collected as follows: (1) IL-1 CM and SHAM CM were collected from HEC monolayers pretreated with and without rIL-1$\beta$ for 4 h, washed, and incubated in RPMI+FCS for a subsequent 5 h (ENDOTHELIAL CM), or (2) RPMI+FCS was incubated with and without rIL-1$\beta$ (5U/ml, 9h) in gelatin-coated Petri dishes without endothelial cells (CELL-FREE CM). $^{111}$In-labeled PMN were diluted in unincubated RPMI+FCS (FRESH MEDIUM), SHAM, and IL-1 CM CELL-FREE CM or ENDOTHELIAL SHAM CM and IL-1 CM ($2 \times 10^6$ cell/ml) for a standard monolayer adhesion assay (see Example 5). In addition, rIL-$\beta$ (5U/ml) was added directly to an aliquot of ENDOTHELIAL SHAM CM immediately prior to assay. PMN adhesion to washed, unactivated (solid bars) or activated (hatched bars) (5 U/ml rIL-$\beta$, 4h) HEC monolayers was assessed. Values are expressed as mean $\pm$ standard deviation for triplicate determinations in this representative experiment. Similar results were obtained in two additional experiments. (*P<0.01 IL-CM compared to SHAM CM).

To test the hypothesis that stimulated endothelial cells contain an inhibitor of PMN-endothelial adhesion, conditioned media were collected from endothelial cell cultures grown in 100 mm dishes. The HEC were washed to remove culture media and incubated in RPMI+FCS with and without IL-1 for 4 h, at which point the HEC were washed again. After incubation for an additional 5 h in fresh RPMI+FCS, IL-1 CM and SHAM CM were collected. PMN adhesion to hyperadhesive HEC monolayers (pretreated with 2.5–5 U/ml rIL-1β, 4 h) was significantly inhibited in the presence of IL-1 CM ($72\pm6\%$, n=10, P<0.001), as compared to SHAM CM (FIG. 2). SHAM CM, to which rIL-1β (5 U/ml) was added after collection, had no inhibitory effect. Incubation of rIL-1β (5 U/ml)-containing medium, in the absence of endothelial cells, did not result in the generation of inhibitory activity.

Acetylsalicylic acid (500 μM) treatment of the HEC did not alter LAI production (90–97% of LAI activity from untreated HEC, three experiments) under conditions which ablated constitutive and calcium ionophore-stimulated $PGI_2$ production. Similar results were obtained with indomethacin pretreatment, indicating that arachidonic acid metabolism via the cyclooxygenase pathway was not required for generation of LAI activity. However, treatment of HEC with actinomycin D (5 μg/ml) for 30 minutes prior to stimulation with rIL-1 (2.5–5 U/ml, 4 h), essentially blocked subsequent LAI production (0–10% of LAI activity from untreated HEC, 6 experiments). Comparable amounts of LAI activity were detected in IL-1 CM collected in protein-free RPMI medium ($65\pm4\%$ LAI activity, 4 experiments), in serum-free, TIS-supplemented medium ($58\pm3\%$ of LAI activity, 10 experiments), and in BSA-supplemented medium ($57\pm6\%$ LAI activity, 5 experiments).

The above observations suggest that de novo protein synthesis is required in the generation of LAI activity by the cytokine-stimulated endothelial cell and, further, that LAI activity does not result from the metabolism of some exogenously added medium component (e.g., a serum factor or IL-1).

In addition to human recombinant IL-1β, and natural human monocyte-derived IL-1, human recombinant IL-1α (10 U/ml), human recombinant TNF (100 U/ml), and bacterial LPS (1 µg/ml) also induced the generation of LAI activity by HEC monolayers, as can be seen below in Table One.

TABLE One

Stimulators of LAI Production by Cultured Human Endothelial Cells

| Mediator | Percent inhibition of PMN Adhesion |
|---|---|
| hm-IL-1 (5 U/ml) | 72 ± 6 |
| rIL-1α (10 U/ml) | 58 ± 7 |
| rIL-1β (2.5 U/ml) | 69 ± 10 |
| (+ Polymyxin B) | 66 ± 7 |
| (+ Heat) | 7 ± 13 |
| LPS (1 µg/ml) | 39 ± 8 |
| (+ Polymyxin B) | 12 ± 3 |
| (+ Heat) | 33 ± 5 |
| rTNF (200 U/ml) | 54 ± 4 |
| IFN γ (200 U/ml) | −1 ± 9 |
| GM-CSF (200 ng/ml) | −1 ± 15 |
| IL-2 (500 U/ml) | −9 ± 9 |

Confluent monolayers were treated for 4 h in RPMI + FCS with the various mediators indicated, washed, and incubated 5 h in RPMI + FCS. Conditioned media were collected and assayed (without dilution) in a standard monolayer cell adhesion assay against washed IL-1-treated (5 U rIL-1β, 4 h) HEC monolayers. Data are presented as mean ± SEM.

Polymyxin B sulfate (20 µg/ml) treatment neutralized the stimulatory effect of LPS but did not reduce the effect of rIL-1β. In contrast, rIL-2 (100 U/ml), rIFN-γ (200 U/ml), and GM-CSF (200 U/ml) did not stimulate LAI production. In addition, the LAI activity in IL-1 CM also inhibited PMN adhesion to HEC monolayers activated with TNF (200 U/ml, 4 h) and LPS (1 µg/ml, 4 h) as detailed in Table Two, below. Similarly, TNF- and LPS-conditioned medium also inhibited PMN adhesion to IL-1, TNF-, and LPS-activated endothelial monolayers.

Conditioned medium from IL-1-stimulated HEC produced comparable inhibition of PMN adhesion to HEC target monolayers activated with TNF (200 U/ml, 4 h; 54±4%, 5 experiments), LPS (1 µg/ml, 4 h; 56±7%, 3 experiments), or IL-1 (2.5 U/ml, 4 h; 68±4, 5 experiments) (see Table Two, below). In contrast, IL-1 CM did not inhibit PMN adhesion to plastic surfaces coated with fresh human serum (4±3% inhibition, 4 experiments), decomplemented human serum (−10±4%, 3 experiments) or zymosan-activated human serum (−8±10%, 3 experiments). These results, taken together with the lack of effect on PMN adhesion to unactivated endothelial cells, suggest that LAI acts to preferentially inhibit leukocyte interaction with the "hyperadhesive" endothelial cell surface.

TABLE Two

LAI Activity from Cytokine- and Endotoxin-Stimulated HEC Assayed on Cytokine- and Endotoxin-Activated HEC Monolayers

| Source of LAI Activity* | Percent Inhibition of PMN Adhesion to Activated HEC | | |
|---|---|---|---|
| | IL-1 | TNF | LPS |
| IL-1 CM | 68 ± 4 | 54 ± 4 | 56 ± 7 |
| TNF CM | 45 ± 9 | 38 ± 9 | 36 ± 8 |
| LPS CM | 39 ± 8 | 31 ± 7 | 12 ± 3 |

*Conditioned media (CM) were collected from cytokine- and endotoxin-stimulated HEC monolayers as described in Example 3. Target HEC monolayers were pretreated with rIL-1β (5 U/ml), TNF (200 U/ml), or LPS (1 µg/ml) for 4 h and washed immediately before the addition of $^{111}$In-labeled PMN resuspended in the test medium. PMN adhesion was determined in a quantitative monolayer adhesion assay (Bevilacqua et al., J. Clin. Invest. 76:2003-2011 (1985)) (see Example 5). Data are presented as mean ± SEM for three separate experiments.

Figure 3:
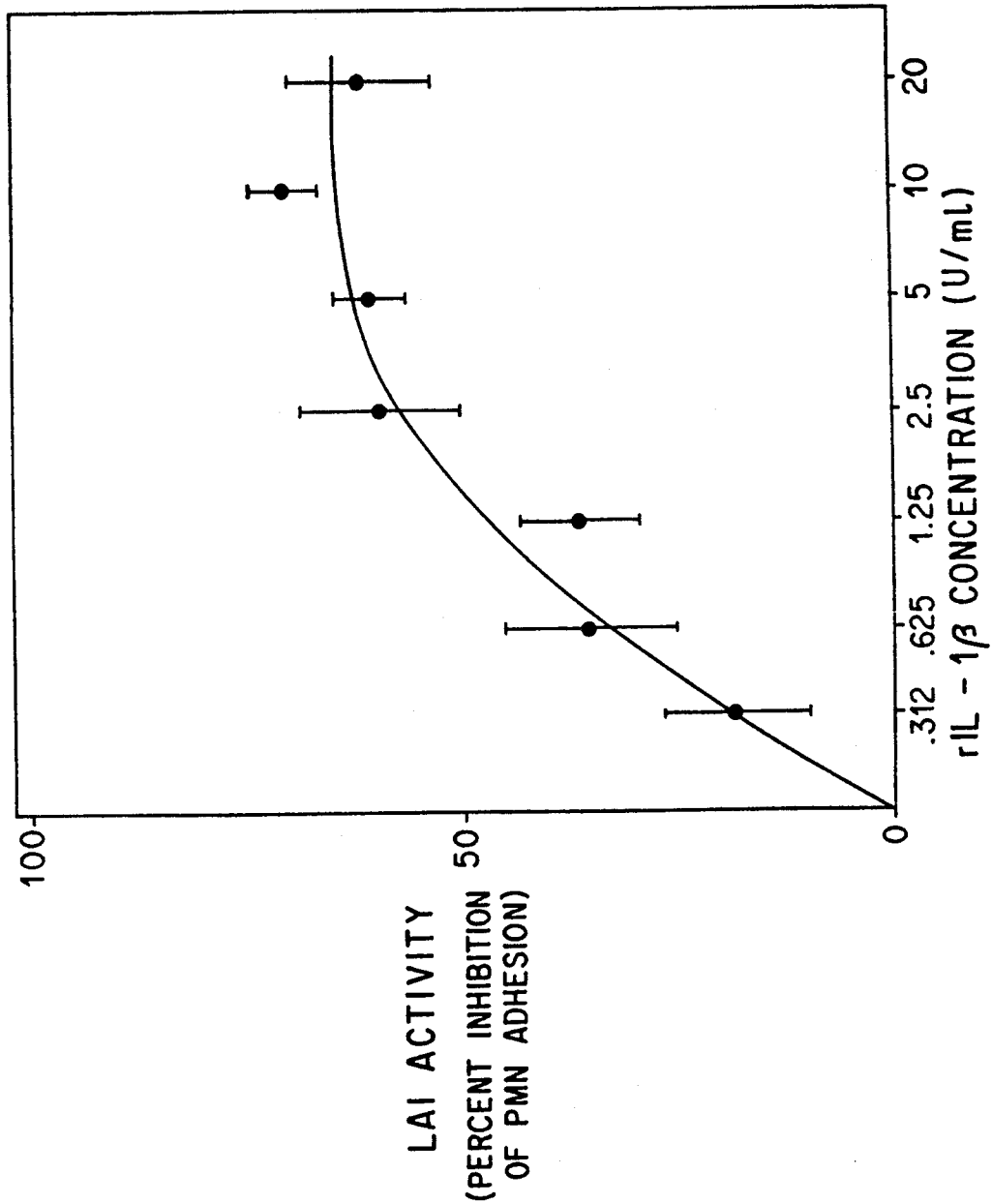
FIG. 3: Concentration dependence on IL-1 stimulation of human vascular endothelial generation of LAI is depicted. Confluent HEC monolayers were pretreated for 4 h with increasing concentrations of hmIL-1 or rIL-1$\beta$, washed, and incubated an additional 5 h in RPMI+FCS. IL-1 CM and SHAM CM were collected and assayed for LAI activity in a standard monolayer adhesion assay. Percent inhibition of PMN adhesion was calculated as described in Example 7. Each point represents the mean $\pm$ SEM of three separate experiments.

Generation of LAI activity was found to be IL-1 concentration-dependent with threshold at 0.1 U/ml rIL-1β and maximal at 2.5–5 U/ml (FIG. 3). The appearance of LAI in the IL-1 CM was time-dependent with inhibitory activity, in media collected at 1 h intervals, detectable at 1–2 h (30±6%, n=5), reaching a maximum at 5–6 h (65±2%) post-IL-1. After 9 hours, a decline in activity was observed (see FIG. 9).

Figure 4:
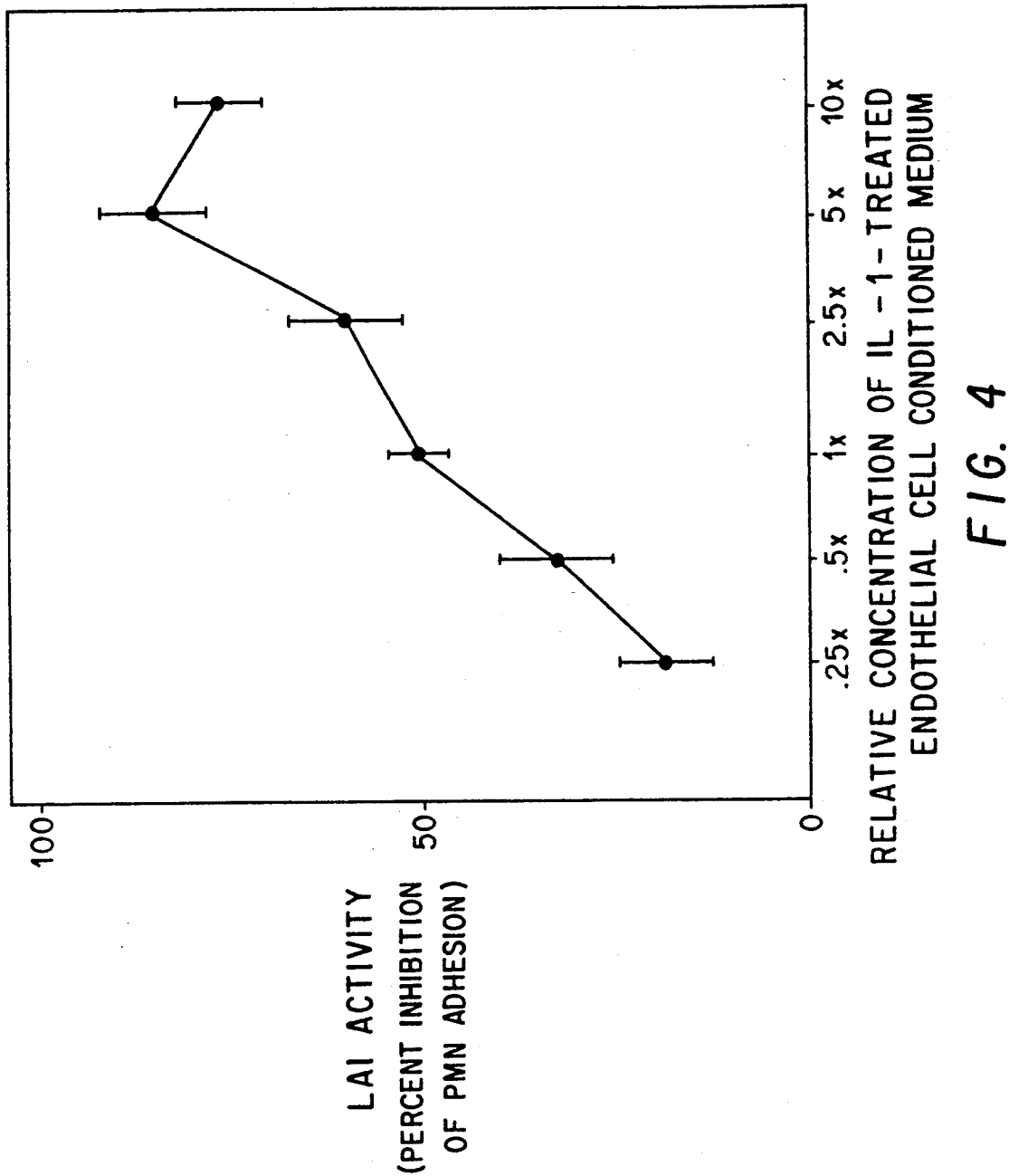
FIG. 4: Concentration dependence on IL-1 CM of LAI-induced inhibition of PMN adhesion is depicted. IL-1 CM was collected in serum-free, TIS-supplemented medium, filtered through an Amicon YM 30 ultrafiltration membrane, and concentrated on an Amicon YM 5 membrane to a 20X concentration (vol/vol). The concentrate was then serially rediluted with RPMI+FCS for assay of LAI, endothelial-derived IL-8 activity. Each point represents mean $\pm$ SEM of five separate experiments.

LAI activity passed freely through an Amicon YM 30 (nominal molecular weight cutoff=30,000), but was concentrated 10–20x on an Amicon YM 5 (nominal molecular weight cutoff=5,000). Inhibition of PMN adhesion was maximally blocked at a 5x concentration of IL-1 CM (75±7% inhibition of PMN adhesion, n=5) (FIG. 4) with proportionately less LAI activity detectable at lower IL-1 CM concentrations.

Example 8

Evaluation of Target of LAI Activity

To determine whether LAI activity exerts its inhibitory effect on the leukocyte or the endothelial cell, each cell type was selectively pretreated. When activated HEC monolayers (5 U/ml rIL-1, 4 h) were incubated for 30 min with IL-1 CM (followed by exchange with fresh medium (1.5 ml)), no inhibition of PMN adhesion was observed (5±8% inhibition, P>0.05, three experiments).

In contrast, when PMN ($3 \times 10^7$ cells in 1.5 ml) were pretreated with IL-1 CM for 30 min, centrifuged (100 x g, 2 min), resuspended in a comparable volume of fresh medium, and added to an activated HEC monolayer, PMN adhesion was significantly inhibited (25±3% inhibition, P<0.001, three experiments). Further, adhesion of unfixed PMN to fixed IL-1-stimulated HEC monolayers (2% paraformaldehyde in PBS, 5 min, 22° C., then stored overnight in PBS+BSA at 4° C.) continued to be significantly inhibited by IL-1 CM (45±9% inhibition, 2 experiments). In contrast, brief fixation of the PMN (2% paraformaldehyde in PBS, 5 min on ice) reduced in the inhibitory effect of LAI by >80%. PMN fixation, per se, did not alter adhesion to untreated or IL-1-treated HEC monolayers. These observations demonstrate that the inhibitory action of LAI is primarily directed at the leukocyte.

Figure 5:
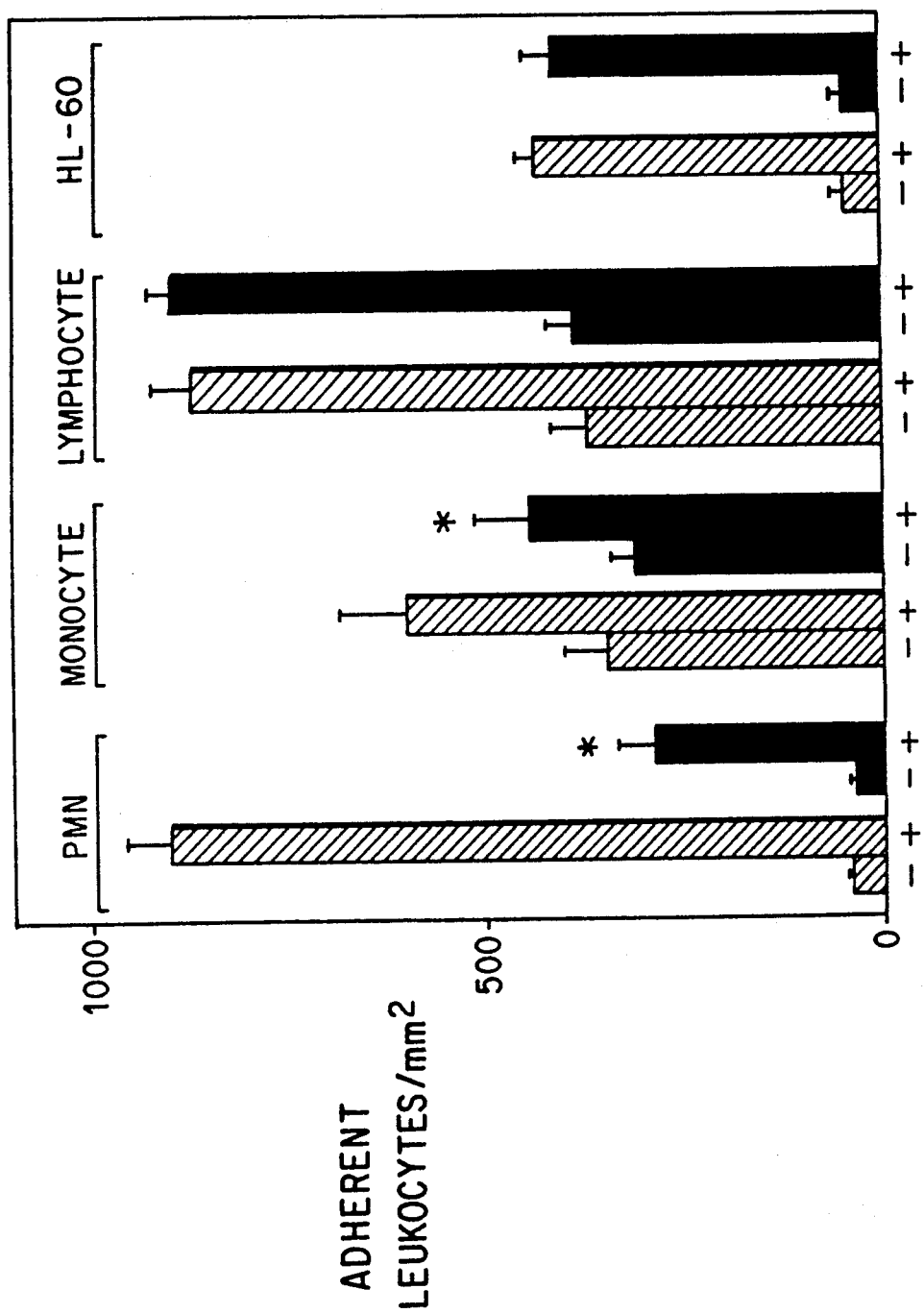
FIG. 5: Effect of LAI on adhesion of different types of leukocytes to untreated and IL-1-treated endothelial cell monolayers is depicted. Isolated radiolabeled PMN, monocytes, lymphocytes, or HL-60 cells were resuspended in SHAM CM (striped bars) or IL-1 CM (solid bars) and adhesion to untreated ($-$) or IL-1-treated ($+$) (2.5 U/ml rIL-1$\beta$, 4 h) HEC was assessed in a 10-minute assay. Values are expressed as mean $\pm$ SEM (*P<0.01 IL-1 CM versus SHAM CM).

As illustrated in FIG. 5, LAI activity appears to differentially affect the adhesion of certain blood leukocytes to cytokine-activated and unactivated endothelium. IL-1 CM consistently produced a marked inhibition of PMN adhesion to activated HEC monolayers (76±4% inhibition of cytokine-stimulated adhesion, P<0.001, 5 experiments), but had no effect on adhesion to activated HEC monlayers was significantly inhibited (55±12% inhibition of cytoline-stimulated adhesion, P<0.01, 5 experiments), while no effect on the relatively extensive adhesion to unactivated monolayers was observed. In contrast, IL-1 CM did not significantly alter the adhesion of peripheral blood lymphocytes (−4±6% inhibition, P>0.1, 3 experiments), HL-60 cells (2±6%, P>0.1, 4 experiments), or U937 (1±9%, P>0.1, 4 experiments) to either IL-1-activated or unactivated HEC monolayers.

Figure 6A:
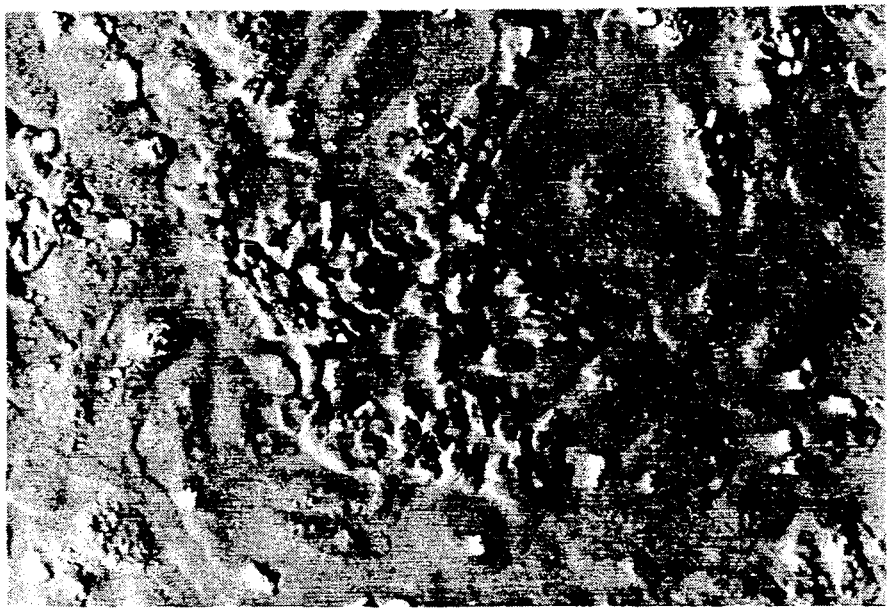
FIG. 6: Hoffman differential-interference contrast microscopy of PMN adhesion to IL-1-treated HEC monolayers is depicted. Isolated PMN were resuspended in SHAM CM (A) or IL-1 CM (B) and added to IL-1-pretreated HEC (2.5 U/ml rIL-1$\beta$, 4 h) for 10 min, and the monolayers washed to remove nonadherent PMN. Note that, in panel B, the adherent PMN are reduced in number and appear less well-spread on the surface of the HEC monolayer. (Original magnification, 400x.)
Figure 6B:
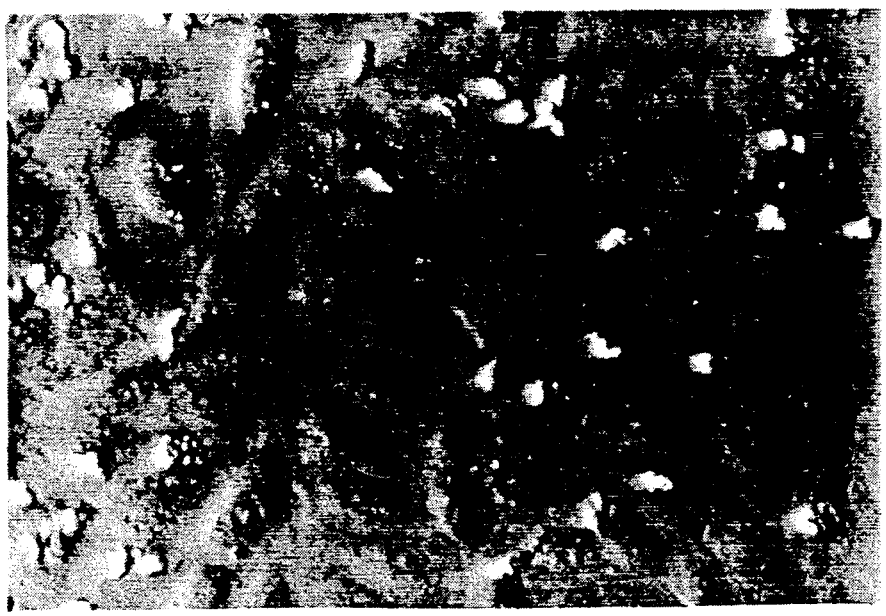
Figure 7A:
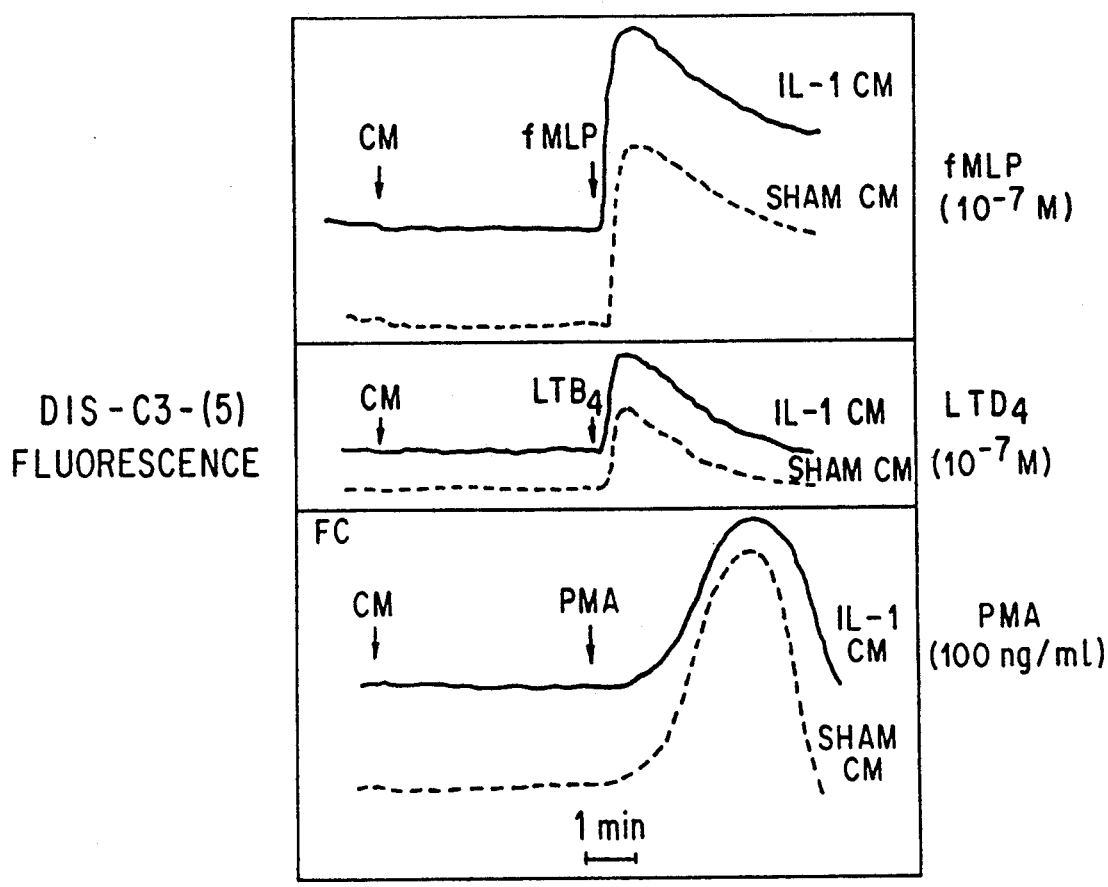
FIG. 7: Agonist-induced membrane depolarization and transient Ca$^{++}$ rise in PMN is depicted.
Figure 7B:
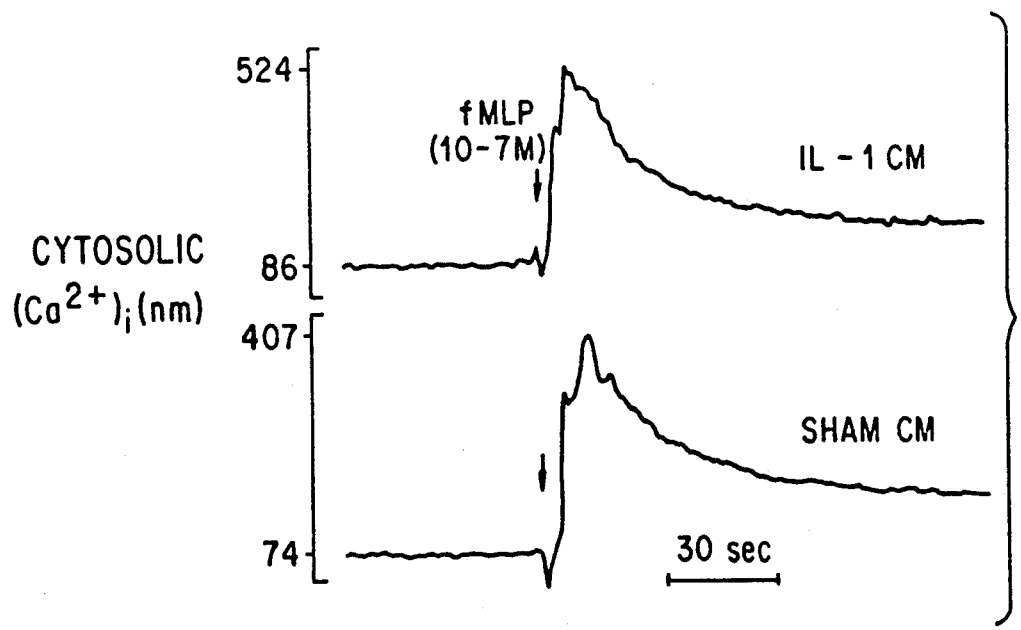

Vital microscopy of PMN adhesion to activated HEC monolayers in the presence and absence of LAI revealed striking differences. In SHAM CM, PMN were tightly adherent in large numbers on the monolayer surface (FIG. 6A). In contrast, the extent of PMN adhesion, in the presence of LAI, was markedly reduced, consistent with the quantitative radiometric assay. Interestingly, although individual PMN had undergone shape change, they did not appear spread on the monolayer surface (FIG. 6B).

Example 9
Assay of PMN Activation

PMN responsiveness to soluble stimuli ($10^{-7}$M FMLP, $10^{-7}$ LTB$_4$, 100 ng/ml PMA) was assessed by quantitative measurement of changes in membrane potential and cytosolic free calcium concentrations.

Changes in membrane potential were evaluated with the fluorescent cyanine probe diSC$_3$-5 (see Whitin et al., *J. Biol. Chem.* 255:1874-1878 (1980); Lazzari et al., *J. Biol. Chem.* 261:9710-9713 (1986)) using a SPEX Fluorolog II spectrofluorimeter with the cuvette compartment controlled at 37° C.

For measurement of Ca$^{++}$-sensitive Fura-2 fluorescence, suspensions of PMN ($10^7$ cells/ml) were resuspended in HBSS without Ca$^{++}$ and Mg$^{++}$ and incubated with Fura-2/AM (stock solution, 1 mM in dimethylsulfoxide) at a final concentration of 1 µM for 10 min at 37° C. The cells were diluted five-fold with HBSS and further incubated for 15 min at 37° C. The cells were washed twice by centrifugation with cold HBSS and stored at 10° C. Immediately prior to assay, cells were pelleted in a Beckman Microfuge (Model B), resuspended in 1.6 ml of warm HBSS plus Ca$^{++}$ and Mg$^{++}$, and allowed to equilibrate in a cuvette for 5 min before addition of agonists.

Fluorescence measurements were made in a SPEX (Edison, N.J.) Fluorolog II (Model CM-1) spectrofluorimeter equipped with a beam splitter, two excitation monochromaters, and a dual-mirror chopping mechanism in a specialized optical configuration to allow rapid alternating (30 Hz) excitation of Fura-2 at two wavelengths, 340 nm and 380 nm. Excitation band widths were set at 6.6 nm. The ratio of emitted fluorescence signals (505 nm, 7.2 nM) permits the calculation of intracellular Ca$^{++}$ concentration which is independent of cell number, dye loading, and dye bleaching. Fluorescence signals were calibrated using 80 µM digitonin to permit equilibration of intracellular and extracellular Ca$^{++}$ (maximum) followed by the addition of 1M TRIS, 300 mM EGTA, pH>10.0 (minimum). The basal and maximum increase in intracellular Ca$^{++}$ were calculated as described in Grynkiewicz et al., *J. Biol. Chem.* 260:3440-3450 (1985). Superoxide generation was determined according to Cohen et al., *J. Clin. Invest.* 61:1081-1088 (1978).

Example 10
Effects of LAI on Other PMN Functions

Stimulus-response signaling and superoxide production in response to soluble inflammatory stimuli were also examined. The addition of IL-1 CM or SHAM CM did not alter resting membrane potential or inhibit membrane depolarization induced by $10^{-7}$M FMLP, $10^{-7}$M LTB$_4$, or 100 ng/ml PMA (FIG. 6A). Similarly, neither IL-1 CM nor SHAM CM altered fMLP-induced rises in cytosolic calcium levels (FIG. 6B). Superoxide production in response to $10^{-7}$M FMLP or 100 ng/ml PMA also was not inhibited by LAI (data not shown). These results indicate that, in the PMN, transduction of activating signals (reflected by membrane depolarization and elevation of cytosolic free calcium) and cellular responses (such as superoxide production) are not inhibited by LAI.

Example 11
Biochemical Characterization

To facilitate preliminary biochemical characterization, LAI was collected from IL-1 activated HEC monolayers in serum-free, transferrin/insulin/selenium-supplemented medium. LAI activity in these preparations was found to be stable to a variety of treatments, including boiling for 20 min, acidification (pH 2 or 4) for 18 h, freezing (−80° C., up to three months), and storage at 4° C. for up to 14 days without the addition of protease inhibitors. LAI activity was non-sedimentable (250,000 x g, 45 min), suggesting that it is soluble, rather than associated with a membrane fragment. LAI activity was not adsorbed by gelatin-agarose or concanavalin-A-agarose. Treatment of IL-1 CM, which had been filtered through a 30,000 molecular weight cutoff membrane, with trypsin (1,000 U/ml, pH 7, 37° C., 18 h), thrombin (2 U/ml, 37° C., 2 h), or heparinase (15 U/ml, 30° C., 2 h), did not affect LAI activity. Treatment with pepsin-linked agarose (4,500 U/ml, pH 4, 37° C., 18 h), however, significantly reduced LAI activity in untreated control. LAI activity was precipitated by ammonium sulfate at 60-80% saturation, and full activity was recovered in this fraction. These results demonstrate that the biological activity of LAI depends on a protein component.

Example 12
Purification of LAI by High-performance Liquid Chromatography HPLC was performed with a Waters Associates (Milford, Mass.) Liquid Chromatography system composed of two model 510 solvent pumps and a programmable Systems Controller gradient maker. Column effluent was monitored at 280 nm with a Waters model 481 absorbance detector. IL-1 CM and SHAM CM in RPMI+TIS were filtered on an Amicon YM 30 membrane, the effluent concentrated 20-40x on a YM 5 membrane (nominal molecular weight cut-off 5,000), dialyzed against distilled H$_2$O (Spectrapor 7, 10,000 molecular weight cut-off, Spectrum Med. Ind., Los Angeles, Calif.), and lyophilized. Lyophilized samples were reconstituted in 0.2M acetic acid, 0.1M triethylamine (pH 3.9) at a concentration of approximately 1 mg/ml, and applied (250 µl sample) to a Waters Protein-PAK 125 gel filtration column (7.8 Mm×30 cm). The column was run as an isochratic system at a flow rate of 1.8 ml/min and 0.9 ml fractions were collected. Fractions were dialyzed 18 h (4° C.) against phosphate buffered saline (136 mM NaCl, 0.3 mM KCl, 0.8 mM Na$_2$HPO$_4$, 0.1 mM KH$_2$PO$_4$, pH 7.4). Fractions were diluted into RPMI+FCS and assayed in a standard monolayer adhesion assay. Protein determinations were performed using Bio-Rad protein reagent (Bio-Rad Laboratories, Richmond, Calif.).

Samples of lyophilized IL-1 CM were fractionated on a Waters Protein-Pak 125 gel filtration column by high-pressure liquid chromatography (as described above). Fractions (0.8 ml) were dialyzed against phosphate buffered saline (pH 7.4), diluted 1:10 in RPMI+FCS and assayed in a standard monolayer adhesion assay. In this system, the peak of LAI activity (fraction 12) was separated from the major protein peak (fraction 9) (see FIG. 8). LAI activity in the peak fraction was present at an effective concentration of 80x as calculated by serial dilution to 50% inhibition of PMN adhesion. The yield of LAI, estimated by serial dilution as activity recovered, was greater than 90%. In preliminary experiments, LAI activity in the peak fraction was stable to boiling and acidification, and was completely destroyed by treatment with pepsin ($-8\pm6\%$ LAI activity in pepsin-treated versus $62\pm10\%$ LAI activity in untreated control).

Example 13

Endothelial Protection Assay

Human endothelial cells were grown to confluency on gelatin coated microtitre wells as previously reported (Wheeler et al. *J. Clin. Invest.* 82:1211 (1988) and Luscinsleas et al. *J. Immunol.* 142:2257 (1989)). The monolayers were then washed twice with medium (RPMI+1% FBS). 100 μl medium +/−10 units/ml rhIL-1β was added to each well and incubated 4 hrs at 37° C. After the IL-1 treatment the monolayers were washed once with medium. Human blood PMN were then added ($2\times10^5$ to $2\times10^6$/well) in 100 μl medium containing test material (for rhIL-8, 1 to 500 nM were tested). The plates were then incubated at 37° C. for time periods ranging from 10 minutes to 2 hrs. After this incubation period, wells were filled with medium, sealed, inverted and spun at 250 g for 5 minutes. The wells were then drained of fluid and fixed by adding 100 μl 2% paraformaldehyde for 15 minutes. Following fixation, wells were stained with Wright's-Geimsa stain and examined microscopically to determine the amount of PMN adherence and extent of damage to the endothelial monolayers. See FIG. 10.

While the invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A method of treating inflammation in a mammalian subject which comprises providing to said subject in need of such treatment a pharmaceutical composition comprising an inflammatory-reducing amount of endothelial-derived IL-8 substantially free of natural contaminants and a pharmaceutically acceptable carrier.

2. A method for protecting against neutrophil mediated damage to endothelial cells comprising:
establishing an effective concentration of endothelial-derived IL-8 substantially free of natural contaminants in the vicinity of said endothelial cells sufficient to inhibit neutrophil mediated damage.

3. A method for protecting against neutrophil mediated damage to endothelial cells comprising:
treating neutrophils with an effective concentration of endothelial-derived IL-8 substantially free of natural contaminants to inhibit neutrophil mediated damage to said endothelial cells.

4. The method of claim 1, wherein said composition is administered intravenously.

5. The method of claim 2, wherein said effective concentration is achieved by intravenous administration to a mammal.

6. The method of claim 3, wherein said effective concentration is achieved by intravenous administration to a mammal.

* * * * *